(12) United States Patent
Sakai et al.

(10) Patent No.: US 8,427,533 B2
(45) Date of Patent: Apr. 23, 2013

(54) IMAGE PICKUP APPARATUS, ELECTRONIC ENDOSCOPE, AND LENS UNIT

(75) Inventors: Seiji Sakai, Chofu (JP); Tomoaki Yamashita, Tokyo (JP); Masahiro Kawauchi, Fuchu (JP); Takahiko Mitani, Hachioji (JP); Yuuya Ishida, Hachioji (JP); Seiji Iwasaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1166 days.

(21) Appl. No.: 12/333,679

(22) Filed: Dec. 12, 2008

(65) Prior Publication Data

US 2009/0185032 A1  Jul. 23, 2009

(30) Foreign Application Priority Data

Dec. 19, 2007  (JP) ................. 2007-327726
Jul. 10, 2008  (JP) ................. 2008-180538

(51) Int. Cl.
*H04N 7/18* (2006.01)

(52) U.S. Cl.
USPC ................. 348/65; 348/68; 348/76

(58) Field of Classification Search ........ 348/72; 600/117, 145, 164, 167, 168, 172, 920; 359/699, 359/379–380, 383
See application file for complete search history.

(56) References Cited

U.S. PATENT DOCUMENTS

| | | | | |
|---|---|---|---|---|
| 4,777,524 A | * | 10/1988 | Nakajima et al. | 348/76 |
| 7,294,102 B2 | * | 11/2007 | Jones et al. | 600/151 |
| 2004/0097791 A1 | * | 5/2004 | Tokuda et al. | 600/173 |
| 2007/0100209 A1 | * | 5/2007 | Takahashi | 600/167 |
| 2007/0149855 A1 | * | 6/2007 | Noguchi et al. | 600/168 |
| 2007/0236782 A1 | | 10/2007 | Sano | |
| 2008/0021279 A1 | * | 1/2008 | Takahashi | 600/151 |

FOREIGN PATENT DOCUMENTS

| | | |
|---|---|---|
| JP | 05-341209 | 12/1993 |
| JP | 2000-206423 | 7/2000 |
| JP | 2002-207178 | 7/2002 |
| JP | 2007-229155 | 9/2007 |
| WO | WO 2007/018086 A1 | 2/2007 |

OTHER PUBLICATIONS

Extended Partial European Search Report dated Oct. 21, 2010.
Chinese Office Action dated Apr. 23, 2010.

* cited by examiner

*Primary Examiner* — Roberto Velez
*Assistant Examiner* — Abdelaaziz Tissire
(74) *Attorney, Agent, or Firm* — Scully, Scott, Murphy & Presser, P.C.

(57) ABSTRACT

An image pickup apparatus of the present invention varies optical properties by moving a part of lenses of an objective lens, and includes a solid-state image pickup device unit that is disposed at a rear-end section and that subjects a subject image to photoelectric conversion, a fixed lens frame that retains the objective lens that is disposed in front of the solid-state image pickup device unit, a movable lens frame that retains the part of lenses that moves along a photographing optical axis O inside the lens frame, and an actuator having one end connected to the movable lens frame and that moves the movable lens frame forward and backward. The actuator includes a rigid member provided so as to extend to the vicinity of the rear end at which the solid-state image pickup device unit is disposed and a shape memory alloy that is coupled to the rigid member.

2 Claims, 24 Drawing Sheets

IMAGE PICKUP APPARATUS, ELECTRONIC ENDOSCOPE, AND LENS UNIT

This application claims benefit of Japanese Applications No. 2007-327726 filed in Japan on Dec. 19, 2007 and No. 2008-180538 filed in Japan on Jul. 10, 2008, the contents of which are incorporated by this reference.

BACKGROUND OF THE INVENTION

1. Field of the Invention

The present invention relates to an image pickup apparatus that varies optical properties that is arranged in an endoscope, an electronic endoscope including the image pickup apparatus, and a lens unit in the image pickup apparatus.

2. Description of Related Art

As is well known, electronic endoscopes are widely used for observing and/or treating the inside of (body cavities of) the human body or for examining and/or repairing the inside of industrial plant facilities and the like. In recent years, in some electronic endoscopes, an image pickup apparatus is used that is equipped with a focus function and a zooming function that focus and zoom in on a photographing object by moving an observation optical system in the optical axis direction for photographing.

More specifically, when carrying out endoscopic observation, an apparatus is desired that makes it possible to change optical properties such as the depth of focus, the image forming magnification ratio, and the viewing angle with respect to an observation target region in accordance with the observation site or observation purpose or the like. Recently, an image pickup apparatus (image pickup unit) is known that is configured to enable movement of one or a plurality of optical lenses among an objective lens group included in the image pickup apparatus (image pickup unit) in an optical axis direction, to thus enable adjustment and alteration of the optical properties.

This kind of technology that varies a lens frame for a focusing function of an image pickup apparatus is disclosed, for example, in Japanese Patent Application Laid-Open Publication No. 5-341209. The aforementioned Japanese Patent Application Laid-Open Publication No. 5-341209 discloses technology that moves a lens frame by fixing one end of a coil spring formed by a shape memory alloy (referred to as "SMA" hereinafter) wire to a protruding portion that is integrally formed in a lens frame to which a lens is attached and passing or not passing a current to the coil spring through two lead wires connected thereto.

Further, for example, an endoscope disclosed in Japanese Patent Application Laid-Open Publication No. 2007-229155 utilizes an urging spring and SMA wire as an actuator apparatus for moving forward and backward a movable lens frame that retains a movable lens that varies optical properties to enable a reduction in the size of an image pickup unit having an actuator and thereby reduce the diameter of the distal end portion of an endoscope insertion portion. According to this endoscope, the movable lens frame is moved backward against the urging force of the urging spring when the SMA wire is caused to contract by passing a current thereto, and thereafter when the current being passed to the contracted SMA wire is stopped to cause the SMA wire to expand, the movable lens frame is moved forward by the urging force of the urging spring, to thereby varies the optical properties.

SUMMARY OF THE INVENTION

An image pickup apparatus according to the present invention varies optical properties by moving a part of lenses of an objective lens, and includes: a solid-state image pickup device unit that is arranged at a rear-end section and that subjects a subject image to photoelectric conversion; a fixed lens frame that retains the objective lens that is disposed to the front of the solid-state image pickup device unit; a movable lens frame that retains the part of lenses that moves along a photographing optical axis inside the lens frame; and an actuator that has one end connected to the movable lens frame and that moves the movable lens frame forward and backward, and that includes a rigid member provided so as to extend as far as a vicinity of a rear end at which the solid-state image pickup device unit is disposed, and a shape memory alloy that is coupled to the rigid member.

An electronic endoscope according to the present invention has an insertion portion that is inserted into a subject/object to be examined and an image pickup apparatus that varies optical properties by moving a part of lenses of an objective lens that is contained in the insertion portion, and observes inside a subject/object to be examined by means of the image pickup apparatus, wherein the image pickup apparatus includes a solid-state image pickup device unit that is arranged at a rear-end section and that subjects a subject image to photoelectric conversion; a fixed lens frame that retains the objective lens that is disposed to the front of the solid-state image pickup device unit; a movable lens frame that retains the part of lenses that moves along a photographing optical axis inside the lens frame; and an actuator that has one end connected to the movable lens frame and that moves the movable lens frame forward and backward, and that includes a rigid member provided so as to extend as far as a vicinity of a rear end at which the solid-state image pickup device unit is disposed, and a shape memory alloy that is coupled to the rigid member.

A lens unit of the present invention includes a distal end side lens frame that retains a plurality of first optical members; a proximal end side lens frame that is provided in a linked manner with respect to the distal end side lens frame, and that retains a plurality of second optical members having an optical axis that matches an optical axis of first optical members retained in the distal end side lens frame; a movable lens frame that retains third optical members that are disposed between the first optical members of the distal end side lens frame and the second optical members of the proximal end side lens frame, and which moves the third optical members to a distal end side or a proximal end side of the optical axis; a first elastic member having an urging force that moves the movable lens frame in a proximal end direction to dispose the movable lens frame at a first observation position; a second elastic member having an urging force that is greater than the urging force of the first elastic member, and that moves the movable lens frame in a distal end direction to dispose the movable lens frame at a second observation position; a pressing member that is moved in a distal end direction by the urging force of the second elastic member; a contact member that is fixed to a distal end portion of the pressing member and that includes a distal end face that contacts against the movable lens frame; a guide pipe that has a distal end face against which a proximal end face of the contact member contacts, and that includes an inner hole in which the second elastic member and the pressing member are slidingly arranged, the guide pipe being integrally fixed to the proximal end side lens frame and setting a movement distance of the contact member; and a shape memory alloy wire that is fixed to the contact member via the inside of the guide pipe, and that has properties whereby a temperature thereof is varied to a predetermined temperature by an electric current that is applied from an external power source to control expanding and contracting thereof, wherein the shape memory alloy wire is in a non-tensile state at a time of expansion, and when contracted the shape memory alloy wire moves the pressing member to which is fixed the contact member that contacts against the movable lens frame to the proximal end side against the urging force of the second elastic member, and also retains the contact member at a position at which the proximal end face of the contact member is separated by a predetermined distance from the distal end face of the guide pipe and the distal end face of the contact member is separated by a predetermined distance from the movable lens frame that is moved to the first observation position.

The above and other objects, features and advantages of the invention will become more clearly understood from the following description referring to the accompanying drawings.

DETAILED DESCRIPTION OF PREFERRED EMBODIMENTS

Hereunder, the present invention is described using embodiments based on the attached drawings.

First Embodiment

Figure 1:
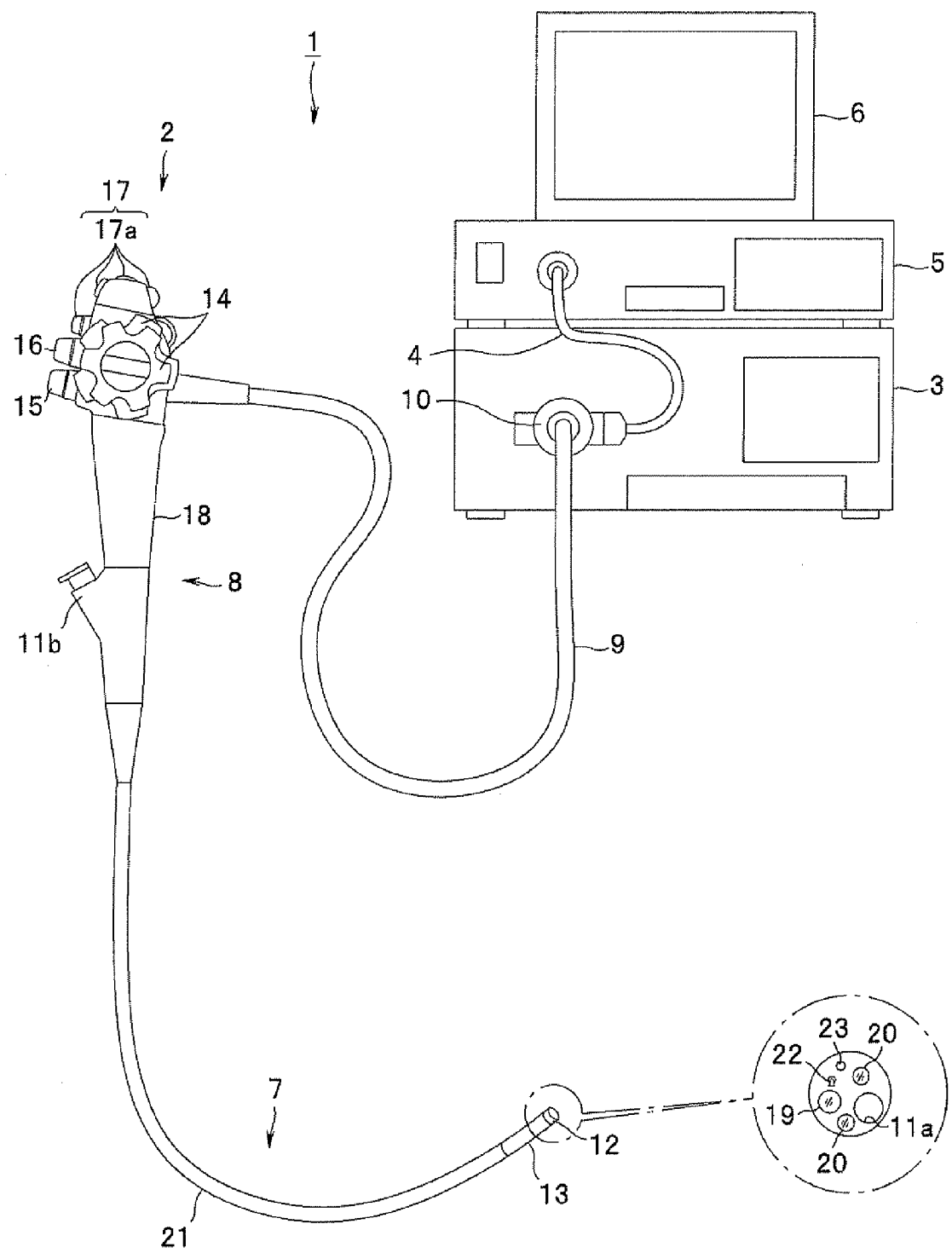
FIG. 1 is a configuration diagram showing an entire electronic endoscope system according to a first embodiment of the present invention.
Figure 2:
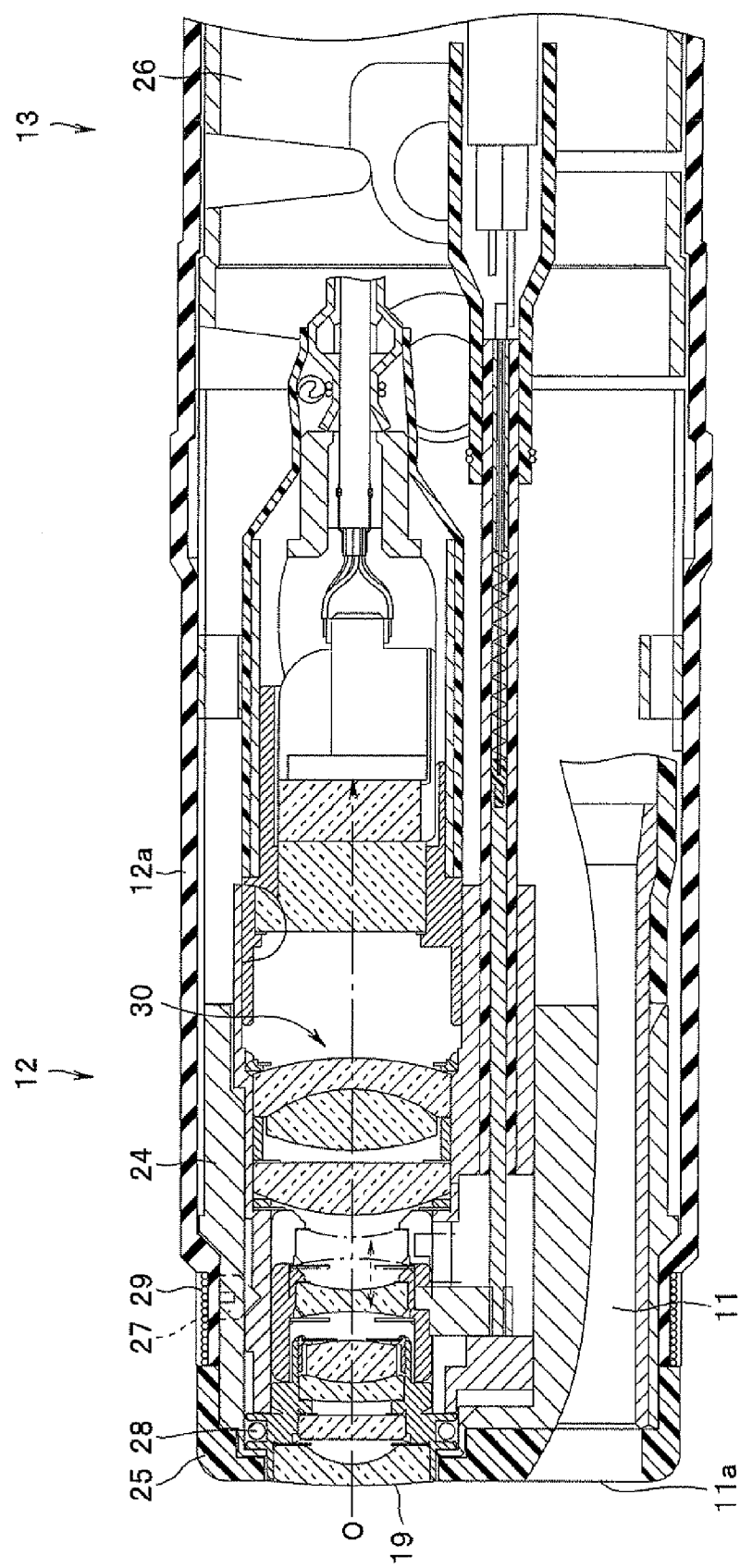
FIG. 2 is a sectional view showing the internal configuration of a distal end portion of an endoscope according to the first embodiment.
Figure 3:
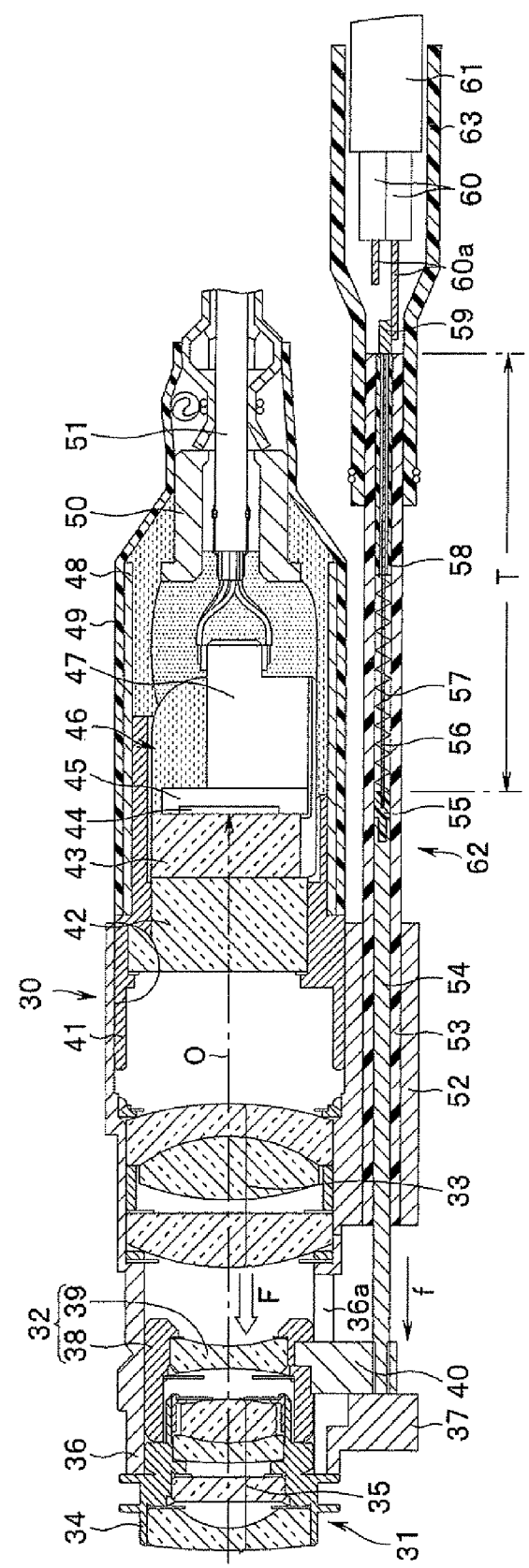
FIG. 3 is a sectional view showing the configuration of an image pickup apparatus according to the first embodiment.
Figure 4:
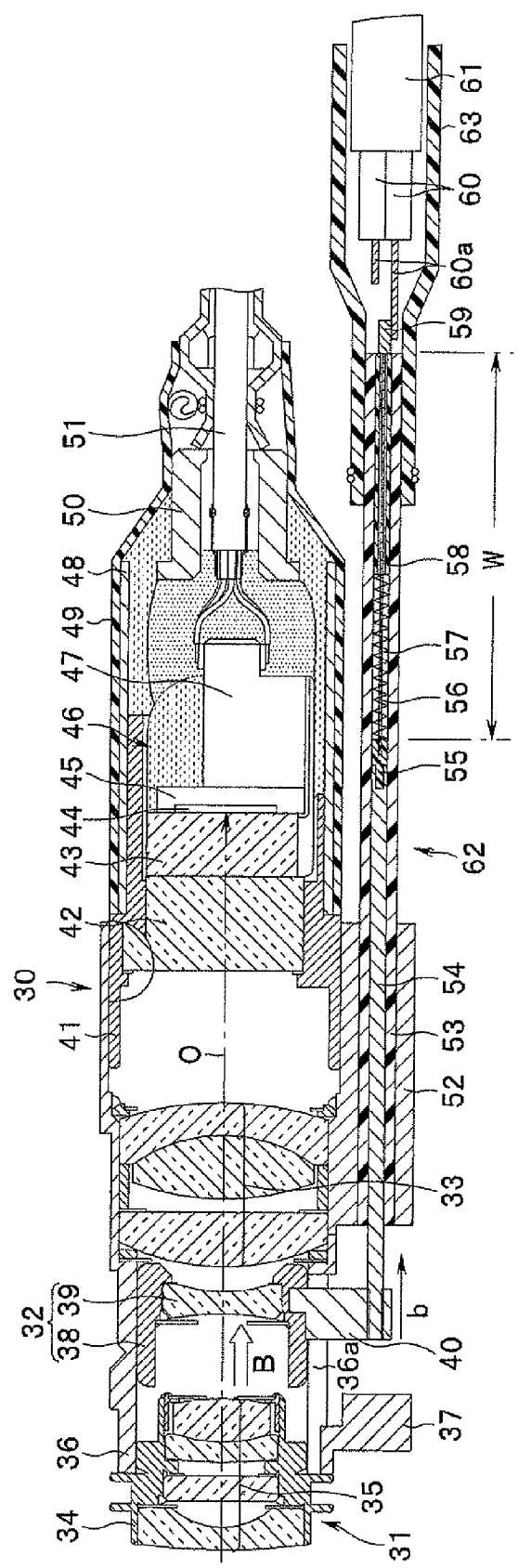
FIG. 4 is a sectional view of the image pickup apparatus that shows a state in which the position of a movable lens frame has been moved from a position shown in FIG. 3 according to the first embodiment.
Figure 5:
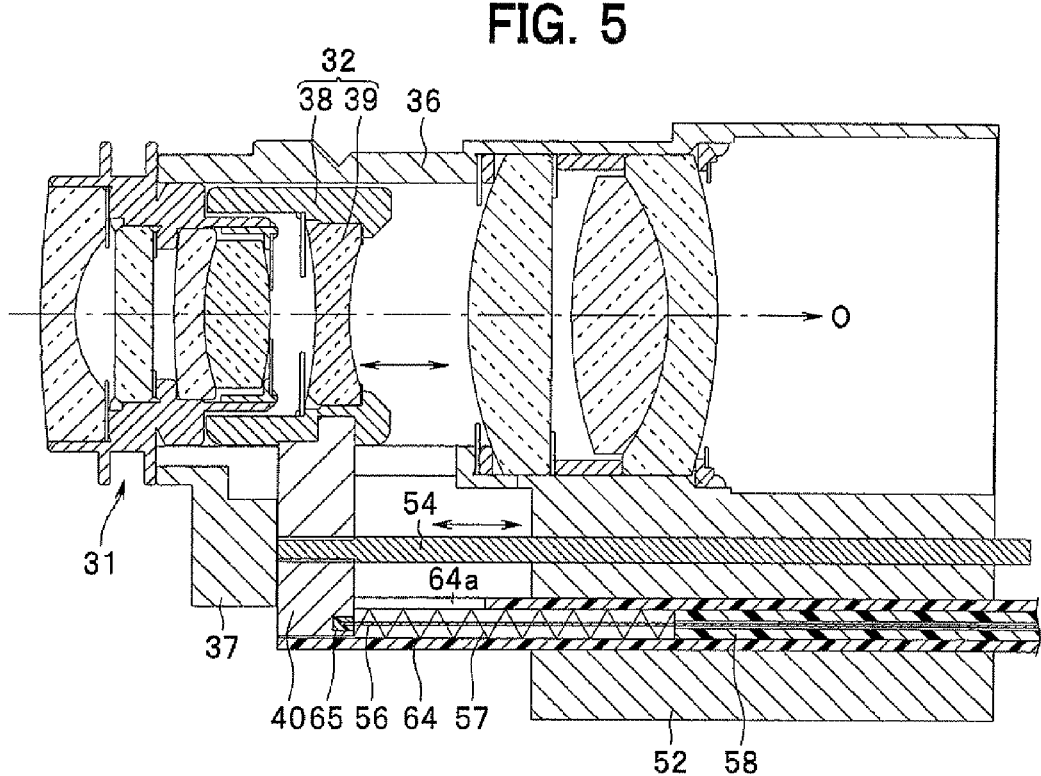
FIG. 5 is a partial sectional view showing the configuration of an image pickup apparatus according to a first modification example of the first embodiment.
Figure 6:
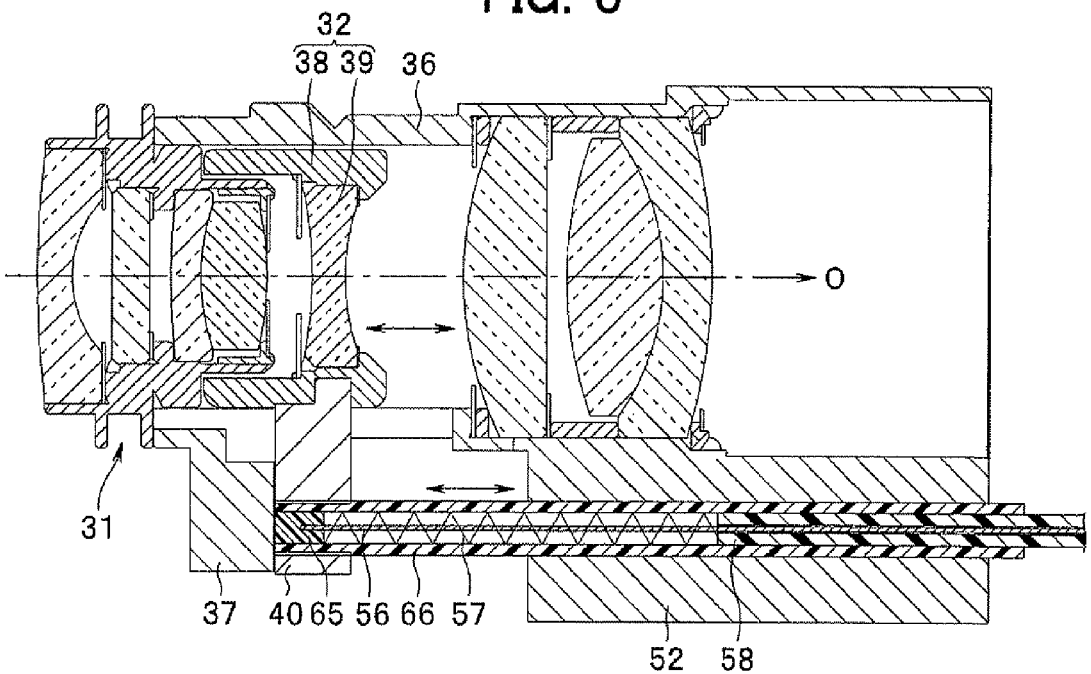
FIG. 6 is a partial sectional view showing the configuration of an image pickup apparatus according to a second modification example of the first embodiment.

First, the present invention is described using FIG. 1 to FIG. 6. FIG. 1 to FIG. 6 relate to the first embodiment of the present invention. FIG. 1 is a configuration diagram showing an entire electronic endoscope system. FIG. 2 is a sectional view showing the internal configuration of a distal end portion of an endoscope. FIG. 3 is a sectional view showing the configuration of an image pickup apparatus. FIG. 4 is a sectional view of the image pickup apparatus that shows a state in which the position of a movable lens frame has been moved from a position shown in FIG. 3. FIG. 5 is a partial sectional view showing the configuration of an image pickup apparatus according to a first modification example. FIG. 6 is a partial sectional view showing the configuration of an image pickup apparatus according to a second modification example.

An electronic endoscope system 1 (hereunder, referred to simply as "endoscope system") of the present embodiment includes an electronic endoscope (hereunder, referred to simply as "endoscope") 2, a light source 3, a video processor 5, and a color monitor 6 that are electrically connected.

The endoscope 2 has an insertion portion 7 and an operation portion 8 from which the insertion portion 7 extends. A universal cord 9 extending from the operation portion 8 is connected to the light source 3 via a scope connector 10. An electrical connector at one end portion of a scope cable 4 is detachably connected to the scope connector 10. An electrical connector at the other end portion of the scope cable 4 is connected to the video processor 5.

The insertion portion 7 includes, in order from the distal end thereof, a distal end portion 12, a bending portion 13, and a flexible pipe portion 21 that are provided in a linked condition. At the distal end face of the distal end portion 12 are arranged a distal end opening portion 11a, an observation window 19, two illumination windows 20, an observation window cleaning opening 22, and an observation object cleaning opening 23.

On the rear face side of the observation window 19 is disposed an image pickup apparatus, described later, that is contained inside the distal end portion 12. Further, an unshown light guide bundle is provided at the rear face side of the two illumination windows 20. The light guide bundle passes through the inside of a universal cord 9 from the distal end portion 12 to transmit an illumination light from the light source 3.

The observation window cleaning opening 22 and the observation object cleaning opening 23 are opening portions of two unshown cleaning tubes that are inserted through the inside of the universal cord 9 from the distal end portion 12. These cleaning tubes are connected on the light source 3 side to an unshown cleaning tank in which cleaning water is stored and an unshown compressor.

The operation portion 8 includes a forceps opening 11b that is provided at a side section on the lower side, a grip portion 18 at a midway section, two bending operation portions 14 provided on the upper side, an air supply/water supply control portion 15, a suction control portion 16, and a switch portion 17 including a plurality of switches 17a that mainly operates an image pickup function. In this connection, the forceps opening 11b of the operation portion 8 and the distal end opening portion 11a of the insertion portion 7 also constitute opening portions of a treatment instrument channel provided in the insertion portion 7.

Next, the configuration of the distal end portion 12 of the endoscope 2 is principally described using FIG. 2 and FIG. 3.

As shown in FIG. 2, an image pickup apparatus 30 is provided inside the distal end portion 12. The image pickup apparatus 30 is insertedly arranged in a rigid distal end rigid member 24, and is fixed to the distal end rigid member 24 with a set screw 27 from the side surface direction. An O-ring 28 for ensuring watertightness is disposed on the outer circumferential portion of the distal end side of the image pickup apparatus 30. A distal end cover 25 forming the distal end face of the distal end portion 12 is adhesively fixed so as to cover the distal end of the distal end rigid member 24.

In this connection, as described above, the distal end opening portion 11a that is a hole formed in the distal end cover 25 constitutes an opening portion of the treatment instrument channel 11 inside the distal end portion 12. Further, a distal end insertion portion rubber member 12a is provided that integrally covers the outer circumference of the distal end rigid member 24 and a bending piece 26 inside the bending portion 13 so as to form the outside of the distal end portion 12 and the bending portion 13. The distal end outer circumferential portion of the distal end insertion portion rubber member 12a is fixed to the distal end portion 12 by a bobbin winder adhesive portion 29.

Since members such as a cleaning tube and a light guide bundle for illumination that are disposed in the distal end portion 12 have configurations that are known, a description of those members is omitted here.

Next, the configuration of the image pickup apparatus 30 as shown in FIG. 3 and FIG. 4 is described.

The image pickup apparatus 30 of the present embodiment has a configuration in which an internal lens moves forward and rearward to implement a focus function or a zooming function.

The image pickup apparatus 30 is principally constituted by, in order from the distal end thereof, a front group lens frame 34 as a fixed lens frame that retains front group lenses 35 that include a plurality of objective lenses and which is included in a front group lens unit 31, a rear group lens frame 36 as a fixed lens frame that retains rear group lenses 33 that include a plurality of objective lenses, a movable lens frame 38 that is disposed between the lens groups 35 and 33 and which retains a movable lens 39 that is included in a movable lens unit 32, and a solid-state image pickup device unit 46 having a CCD or a CMOS or the like.

The rear end portion of the front group lens frame 34 and the front end portion of the rear group lens frame 36 are joined by fitting the two portions together. A front end portion of a solid-state image pickup device retention frame 41 that retains a solid-state image pickup device unit 46 is insertedly fixed in the rear end portion of the rear group lens frame 36.

The movable lens unit 32 is slidingly disposed along the photographing optical axis O direction within the rear group lens frame 36 at the rearward side of the front group lens unit 31. At the bottom of the movable lens frame 38 of the movable lens unit 32, a connection rod 40 is provided so as to extend downward. The sectional form in the lengthwise direction of the connection rod 40 is a substantially elliptic cylindrical shape.

The solid-state image pickup device unit 46 includes within the solid-state image pickup device retention frame 41, in order from the distal end, two optical members 42 and 43, a solid-state image pickup device chip 45 in which an image area 44 is located at the front face, and a multilayer substrate 47. In this connection, the solid-state image pickup device chip 45 and the multilayer substrate 47 are electrically connected by an FPC.

Further, the multilayer substrate 47 is connected with a plurality of communication lines of a cable 51. The cable 51 is insertedly disposed inside the endoscope 2, and is electrically connected with the video processor 5 via the universal cord 9 and the scope cable 4. A substantially cylindrical cable retention member 50 is externally fitted to the distal end portion of the cable 51.

A reinforcing frame 48 is fitted to the outer circumferential portion at the proximal end of the solid-state image pickup device retention frame 41. A coating member 49 that is a heat-shrinkable pipe that integrally covers the cable retention member 50 as far as the distal end portion of the cable 51 is provided on the outer circumference of the reinforcing frame 48. In this connection, a protective agent such as an adhesive is filled into a space formed by the reinforcing frame 48 and the coating member 49 as far as the cable retention member 50 from the proximal end portion of the solid-state image pickup device retention frame 41 in which the solid-state image pickup device chip 45 is disposed.

Furthermore, at a rear lower portion of the rear group lens frame 36, an actuator retention portion 52 that retains an actuator 62 that configures an actuator apparatus that moves the movable lens unit 32 forward and backward is formed so as to protrude downward.

Next, the configuration of the actuator 62 that is attached to the image pickup apparatus 30 is described.

The actuator 62 includes a long guide pipe 53 that is formed from an insulating member formed of a hard nonmetal that is insertedly disposed in the actuator retention portion 52 of the rear group lens frame 36, a moveable shaft 54 that is a rod-like rigid member that is inserted through the inside of the guide pipe 53 in a condition in which the moveable shaft 54 can move forward and backward, an insulating member 55 that has the same external diameter as the moveable shaft 54 and is connected to the proximal end of the moveable shaft 54, a shape memory alloy wire 56 that is inserted through the inside of the guide pipe 53 and which has a distal end portion connected to the insulating member 55, a pressure spring 57 that constitutes an elastic body as an urging body that is externally fitted on the shape memory alloy wire 56, a spring-stop pipe 58 through which the shape memory alloy wire 56 is inserted and which is constituted by an insulating pipe that is insertedly fitted into the rearward portion of the guide pipe 53, and a block body 59 that fixes the proximal end of the shape memory alloy wire 56 by caulking.

The shape memory alloy wire 56 is a wire with a diameter of several tens of microns that is made from a shape memory alloy (hereunder, referred to as "SMA") that contracts when heated and expands when cooled (hereunder, the shape memory alloy wire is referred to as "SMA wire").

The aforementioned guide pipe 53 is adhesively fixed to the actuator retention portion 52 in a condition in which a distal end position of the guide pipe 53 is disposed in alignment with the distal end face of the actuator retention portion 52. The guide pipe 53 has a length that extends as far as the rear-end section of the image pickup apparatus 30. The guide pipe 53 is precisely fixed so that the longitudinal axis thereof is parallel to the photographing optical axis O in order to realize the optical performance of the image pickup apparatus 30.

Further, the distal end portion of the moveable shaft 54 that is provided so as to be movable in the forward and rearward directions inside the guide pipe 53 is screwed into the connection rod 40. The moveable shaft 54 is shorter than the guide pipe 53, and the proximal end portion thereof is disposed inside the guide pipe 53. The moveable shaft 54 is also precisely set so that a forward/rearward movement axis on which the moveable shaft 54 moves forward and rearward inside the guide pipe 53 is parallel to the photographing optical axis O in order to realize the optical performance of the image pickup apparatus 30.

The SMA wire 56 that is passed through the inside of the guide pipe 53 is folded back at the insulating member 55 that is connected to the proximal end of the moveable shaft 54. One end of the SMA wire 56 that is folded back is fixed by caulking to the block body 59 and the other end thereof is fixed by caulking to an unshown other block body. An unshown insulating tube is covered over the SMA wire 56 on the folded-back side.

The pressure spring 57 that is externally fitted to the SMA wire 56 is arranged between the insulating member 55 and the spring-stop pipe 58 inside the guide pipe 53 so that both ends thereof contact against the insulating member 55 and the spring-stop pipe 58. Since the spring-stop pipe 58 is fixed to the guide pipe 53, the pressure spring 57 urges frontward the insulating member 55 that integrally moves forward and backward with the moveable shaft 54.

The block body 59 that fixes the two ends of the SMA wire 56 as described above has a shape that is larger than the hole diameter of the spring-stop pipe 58, and is arranged in a state in which the block body 59 contacts against the rear end face of the spring-stop pipe 58. The block body 59 is electrically connected by a solder or the like to an element wire 60$a$ of the cable 60 on the application side of an electric cable 61. The other block body, which is unshown, is electrically connected by a solder or the like to the element wire 60$a$ of the cable 60 on the feedback side.

A connecting portion between the block body 59 and the electric cable 61 is covered by an insulating tube 63 that integrally covers the proximal end portion of the guide pipe 53, so that the connecting portion is kept in an insulated state. The electric cable 61 is disposed as far as a scope connector 10 of the universal cord 9 of the endoscope 2, and power that is applied to the electric cable 61 is supplied from the video processor 5 via the scope cable 4.

In this connection, a notch portion 36$a$ that constitutes a guide groove is formed in the rear group lens frame 36 so that the connection rod 40 that is connected to the movable lens unit 32 at a front lower side can move forward and backward. Further, in the rear group lens frame 36 is formed a restriction contact portion 37 that extends in the direction of the lower part of the distal end portion in order to restrict forward movement of the connection rod 40.

Next, the action of the actuator 62 that moves the movable lens unit 32 of the image pickup apparatus 30 of the present embodiment forward/backward with the configuration described above is described.

When driving the actuator 62 of the image pickup apparatus 30 to execute a focus function or a zooming function with respect to a subject using the endoscope 2, an electric current flows to the electric cable 61 from a power source included in the video processor 5 based on a predetermined operation performed at the operation portion 8 of the endoscope 2. Thereupon, the electric current flows into the electric cable 61 and the SMA wire 56, whereby the SMA wire 56 generates heat and contracts from a length T shown in FIG. 3 to a length W shown in FIG. 4.

Thereupon, the moveable shaft 54 is pulled rearward from the state shown in FIG. 3 to the state shown in FIG. 4 together with the insulating member 55 by the SMA wire 56 against the urging force of the pressure spring 57 (in the direction of arrow b in FIG. 4). As a result, the connection rod 40 that is fixed to the distal end of the moveable shaft 54 moves rearward (in the arrow B direction in FIG. 4) while being guided by the notch portion 36a of the rear group lens frame 36 together with the movable lens unit 32. More specifically, the movable lens unit 32 moves from a position at the front side as shown in FIG. 3 to a rearward position as shown in FIG. 4 due to a contraction action caused by heat generation of the SMA wire 56. At this time, the moveable shaft 54 is guided in a straight line that is parallel to the photographing optical axis O that realizes the optical performance of the image pickup apparatus 30 by the guide pipe 53.

In this case, when the flow of electric current to the electric cable 61 is stopped, the SMA wire 56 undergoes natural cooling and returns to the original length (length T shown in FIG. 3). At that time, the insulating member 55 is pushed forward by the urging force of the pressure spring 57. In accompaniment therewith, the moveable shaft 54 and the connection rod 40 that have moved in the proximal end direction are pushed forward while being guided by the notch portion 36a of the rear group lens frame 36. Thereupon, the movable lens unit 32 moves forward in response to the movement of the moveable shaft 54 and the connection rod 40. The forward movement of the connection rod 40 is restricted by the front face thereof contacting against the restriction contact portion 37 of the rear group lens frame 36.

Thus, the actuator 62 that moves the movable lens unit 32 forward and backward has a configuration whereby forward and backward movement of the moveable shaft 54 is implemented using heat contraction of the SMA wire 56 and an urging force of the pressure spring 57.

As described above, in the image pickup apparatus 30 of the endoscope 2 of the present embodiment, the guide pipe 53 that guides in a straight line the moveable shaft 54 that moves forward and rearward of the actuator 62 is arranged to extend as far as the vicinity of the proximal end portion of the image pickup apparatus 30. Therefore, when manufacturing the endoscope 2, the configuration of the image pickup apparatus 30 is such that, after first assembling the distal end rigid member 24, electrical connection of the electric cable 61 to the SMA wire 56 of the actuator 62 can be performed at a rearward position at which there is a relatively large amount of space.

Thus, the endoscope 2 of the present embodiment has a configuration that takes assemblability into consideration so that electrical connection of the actuator 62 of the image pickup apparatus 30 that is mounted to the distal end portion 12 can be performed easily.

Further, in the endoscope 2 of the present embodiment, the rod-like moveable shaft 54 that transmits expansion and contraction of the SMA wire 56 and an urging force of the pressure spring 57 as well as the guide pipe 53 that retains the moveable shaft 54 in a straight line are arranged in a mechanism that moves the movable lens unit 32 forward and backward. Therefore, since a flexible and unstable member such as the SMA wire 56 is not directly connected to the movable lens unit 32, the optical performance of the image pickup apparatus 30 is reliably maintained.

More specifically, for the mechanism that moves the movable lens unit 32 forward and rearward in the image pickup apparatus 30, strict accuracy is required with respect to the position of the photographing optical axis O that passes through the movable lens 39 of the movable lens unit 32. Consequently, accuracy with respect to the components is also required at the time of manufacture. Therefore, according to the present embodiment, if the accuracy of disposing the rigid guide pipe 53 and the moveable shaft 54 in parallel with the photographing optical axis O, and the rectilinear guiding accuracy and rectilinear movement accuracy of these components are reliably maintained, stable rectilinearity can be sufficiently maintained without the position of the photographing optical axis O that passes through the movable lens 39 of the movable lens unit 32 being displaced at the time of forward or backward movement.

In this connection, as a first modification example, as shown in FIG. 5, in order to stabilize the position of the photographing optical axis O passing through the movable lens unit 32 without displacing the position, a configuration may be adopted in which the SMA wire 56 and the moveable shaft 54 of the actuator 62 are parallelly disposed.

More specifically, the moveable shaft 54 connected to the connection rod 40 is independently inserted into and movably retained in a hole portion that is parallel to the photographing optical axis O and formed in the actuator retention portion 52, and is rectilinearly guided thereby. The SMA wire 56 is directly connected to the connection rod 40 via the insulating member 65, and the distal end of the pressure spring 57 contacts against the proximal end face thereof so as to urge the connection rod 40 forward.

The SMA wire 56 and the pressure spring 57 are insertedly disposed in an insulating pipe 64 that has a groove portion 64a notched in the top of the distal end thereof. The spring-stop pipe 58 is insertedly fixed to the rear of the insulating pipe 64. In this connection, the lower end portion of the connection rod 40 is housed in the groove portion 64a of the insulating pipe 64 so as not to obstruct forward or rearward movement thereof.

Even when adopting such a configuration like this, since the moveable shaft 54 is rectilinearly guided by the hole portion of the actuator retention portion 52, a displacement in the position of the photographing optical axis O that passes through the movable lens unit 32 can be prevented.

Further, as a second modification example, as shown in FIG. 6, a configuration may be adopted in which the insulating pipe 66 that is connected to the connection rod 40 is insertedly retained in a moveable condition in a hole portion parallel to the photographing optical axis O that is formed in the actuator retention portion 52.

More specifically, the distal end portion of the insulating pipe 66 is screwed into the connection rod 40. The SMA wire 56 is connected via the insulating member 65 at the inside of the distal end of the insulating pipe 66, and the SMA wire 56 passes through the inside thereof.

Further, although not shown in the drawing, the spring-stop pipe 58 against which contacts the proximal end of the pressure spring 57 that is externally fitted to the SMA wire 56 that is provided inside the insulating pipe 66 is fixed at the rear-end section, so that even if the insulating pipe 66 moves forward or rearward, the position of the spring-stop pipe 58 is fixed. That is, the insulating pipe 66 connected to the connection rod 40 is configured to be moveable forward and backward with respect to the actuator retention portion 52 and the spring-stop pipe 58.

Even when adopting such a configuration like this, similarly to the first modification example, since the moveable shaft 54 is rectilinearly guided by the hole portion of the actuator retention portion 52, a positional displacement of the photographing optical axis 0 passing through the movable lens unit 32 can be prevented.

Second Embodiment

Figure 7:
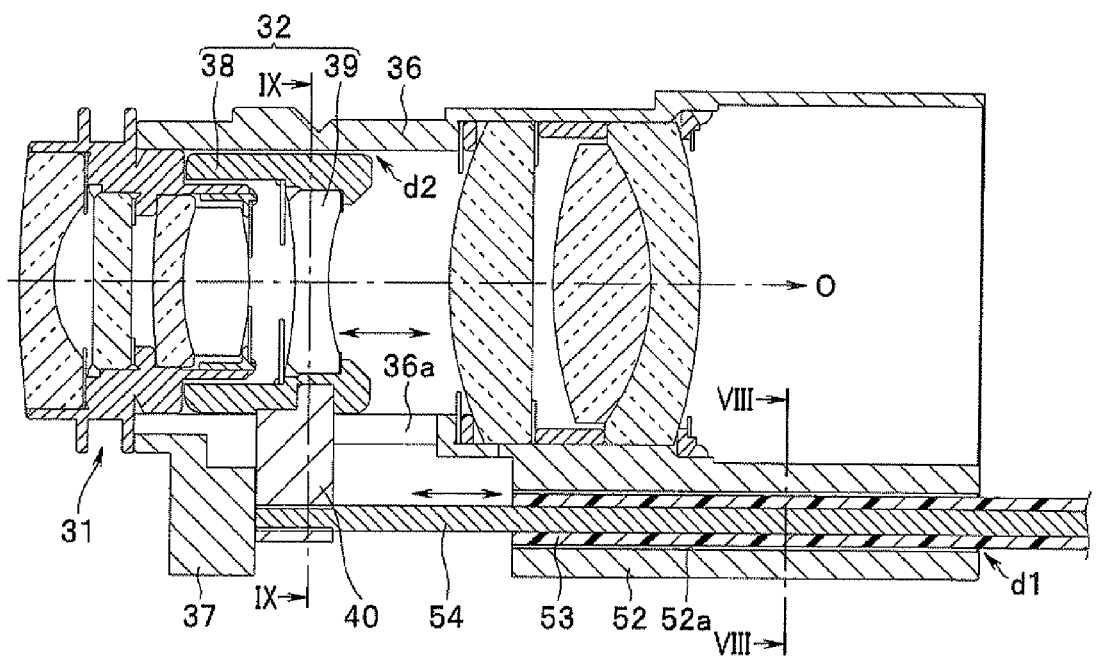
FIG. 7 is a partial sectional view showing the configuration of an image pickup apparatus according to a second embodiment of the present invention.
Figure 8:
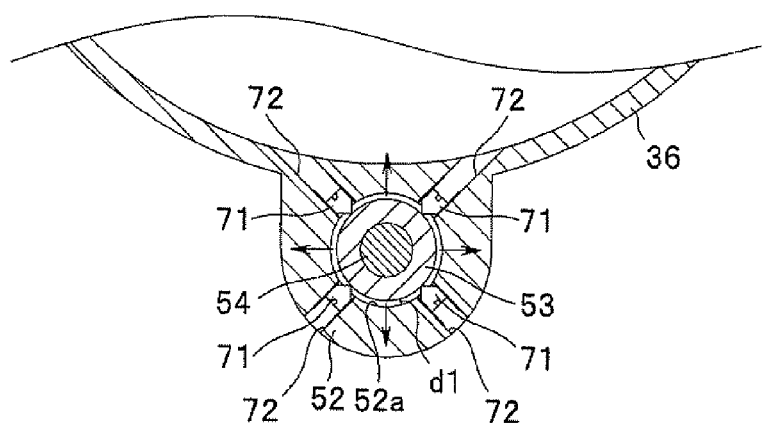
FIG. 8 is a sectional view of the image pickup apparatus according to the second embodiment of the present invention along line VIII-VIII in FIG. 7.
Figure 9:
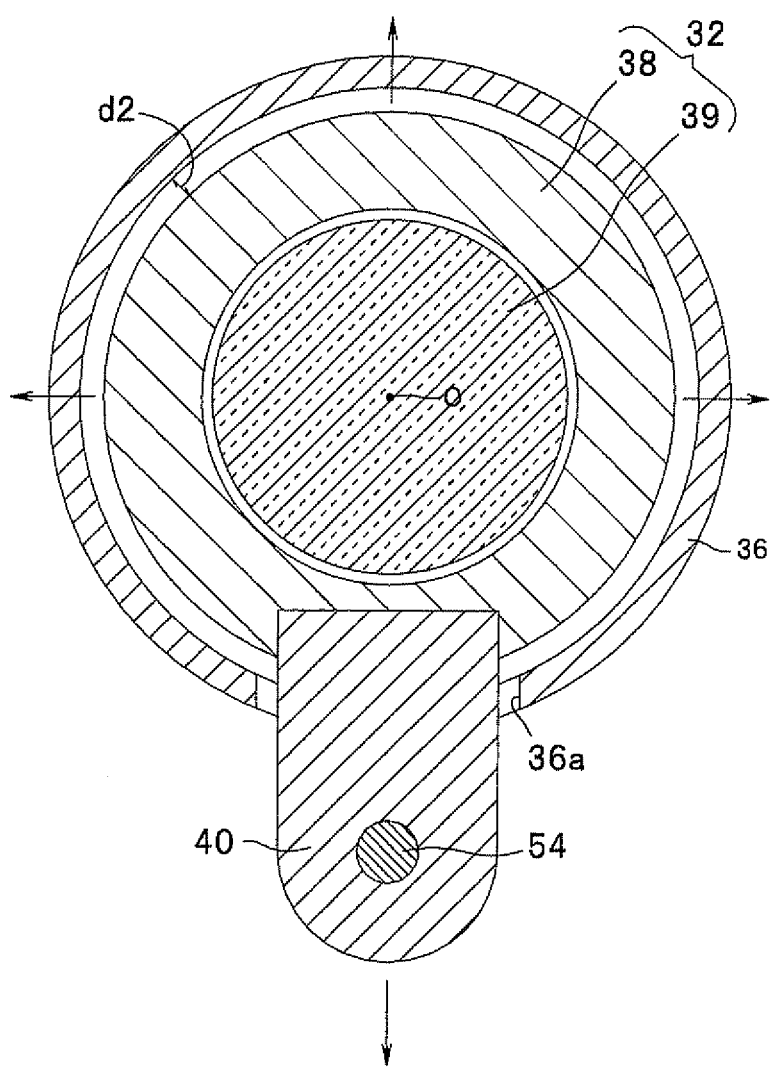
FIG. 9 is a sectional view of the image pickup apparatus according to the second embodiment of the present invention along line IX-IX in FIG. 7.

Next, a second embodiment of the present invention is described referring to FIG. 7 to FIG. 9.

FIG. 7 and FIG. 9 relate to the second embodiment of the present invention. FIG. 7 is a partial sectional view showing the configuration of an image pickup apparatus. FIG. 8 is a sectional view along line VIII-VIII in FIG. 7. FIG. 9 is a sectional view along line IX-IX in FIG. 7. In the following description, the same reference numerals are used for components that are the same as components of the image pickup apparatus 30 of the endoscope 2 of the first embodiment described above, and a detailed description of those components is omitted.

The image pickup apparatus 30 of the present embodiment is configured so that a position along the longitudinal axis direction of the guide pipe 53 of the actuator 62 of the rear group lens frame 36 can be adjusted.

More specifically, as shown in FIG. 7 and FIG. 8, a hole diameter of a hole portion 52a into which the guide pipe 53 is insertedly disposed that is formed in the actuator retention portion 52 is made somewhat larger than the external diameter of the guide pipe 53 to provide a clearance d1 between the outer surface of the guide pipe 53 and an inner circumferential surface forming the hole portion 52a of the actuator retention portion 52.

After the guide pipe 53 is inserted into the hole portion 52a of the actuator retention portion 52, screws 71 as fixing members are respectively screwed into four screw holes 72 that are formed in the rear group lens frame 36 and the actuator retention portion 52, to thereby fix the actuator retention portion 52 from four directions with these screws 71.

Further, as shown in FIG. 9, the external diameter of the movable lens frame 38 is set to allow a clearance d2 to exist between the movable lens frame 38 and the inner diameter of the rear group lens frame 36. That is, the external diameter of the movable lens frame 38 is set to be smaller by the amount of the clearance d2 than the inner diameter of the rear group lens frame 36.

In this connection, the clearance d2 may be the same as the above described clearance d1 between the outer surface of the guide pipe 53 and the inner circumferential surface forming the hole portion 52a of the actuator retention portion 52. Further, as long as the movable lens frame 38 can retain the movable lens 39 even without conforming to the inner surface shape of the rear group lens frame 36, the movable lens frame 38 may be any shape that can move forward and backward inside the rear group lens frame 36 with a clearance equal to or greater than the clearance d2.

In the image pickup apparatus 30 of the present embodiment configured as described above, by adjusting the amount by which the four screws 71 that fix the guide pipe 53 to the actuator retention portion 52 are screwed in, the axial alignment of the movable lens 39 with respect to the photographing optical axis O can be adjusted within a range that is twice the amount of the clearance d1 (d1×2) in any direction of 360 degrees to the top, bottom, left, or right. More specifically, by varying the position of the guide pipe 53, the position of the moveable shaft 54 that is rectilinearly guided by the guide pipe 53 and the position of the connection rod 40 of the movable lens frame 38 that is fixed to the distal end of the moveable shaft 54 are varied.

As described above, in addition to the advantages of the first embodiment, according to the image pickup apparatus 30 of the present embodiment, since axial alignment with the photographing optical axis O of the movable lens 39 can be easily performed, the accuracy requirements for components including the movable lens frame 38 and the connection rod 40 are relaxed, and assembly of the movable lens frame 38 equipped with the movable lens 39 for which accuracy is most required is easy.

Third Embodiment

Next, the third embodiment of the present invention is described based on FIG. 10 to FIG. 14.

Figure 10:
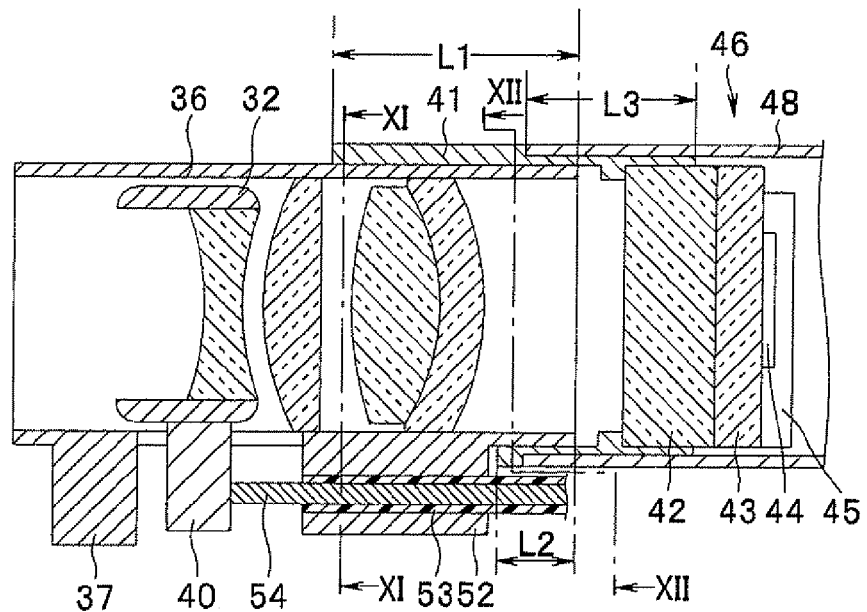
FIG. 10 is a partial sectional view showing the configuration of an image pickup apparatus that is fitted and fixed to a distal end rigid member according to a third embodiment of the present invention.
Figure 11:
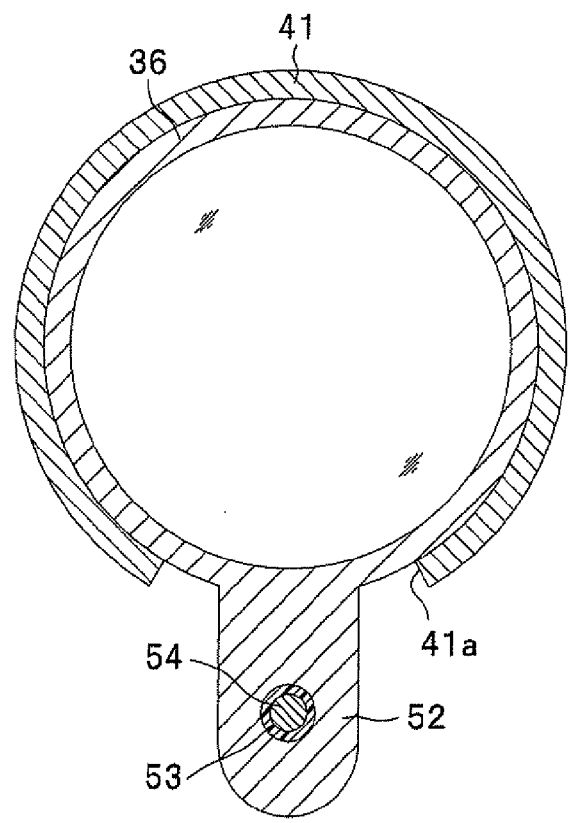
FIG. 11 is a sectional view of the image pickup apparatus according to the third embodiment of the present invention along line XI-XI in FIG. 10.
Figure 12:
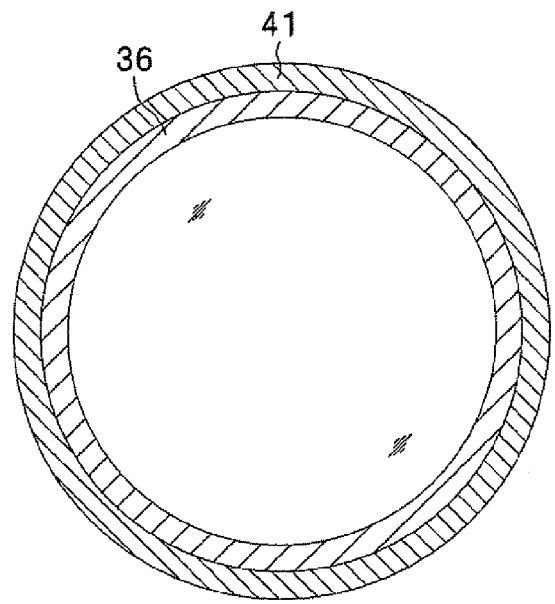
FIG. 12 is a sectional view of the image pickup apparatus according to the third embodiment of the present invention along line XII-XII in FIG. 10.
Figure 13:
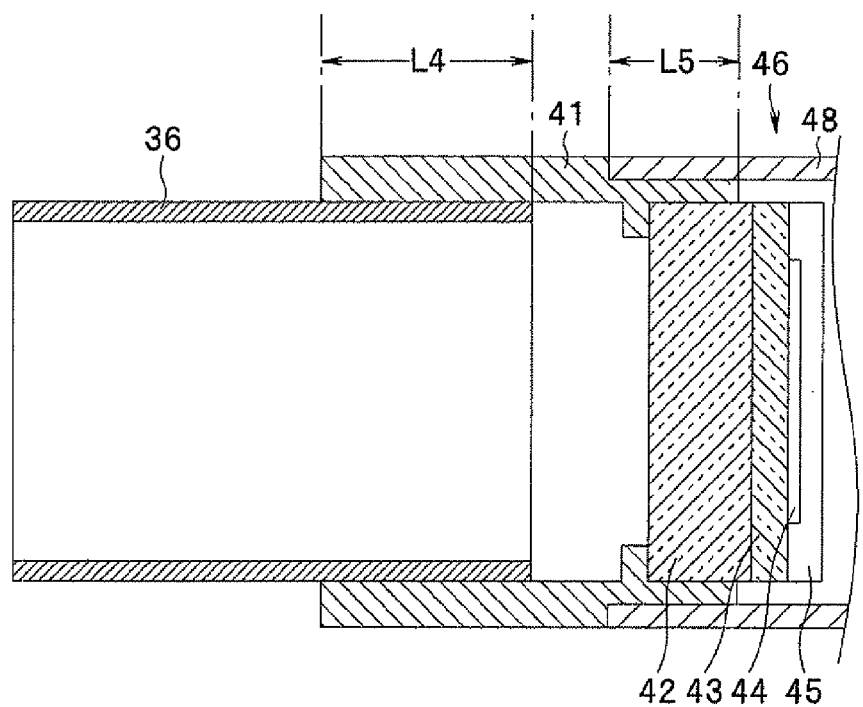
FIG. 13 is a partial sectional view showing the configuration of a conventional image pickup apparatus equipped with a fixed focal length optical system according to the third embodiment of the present invention.
Figure 14:
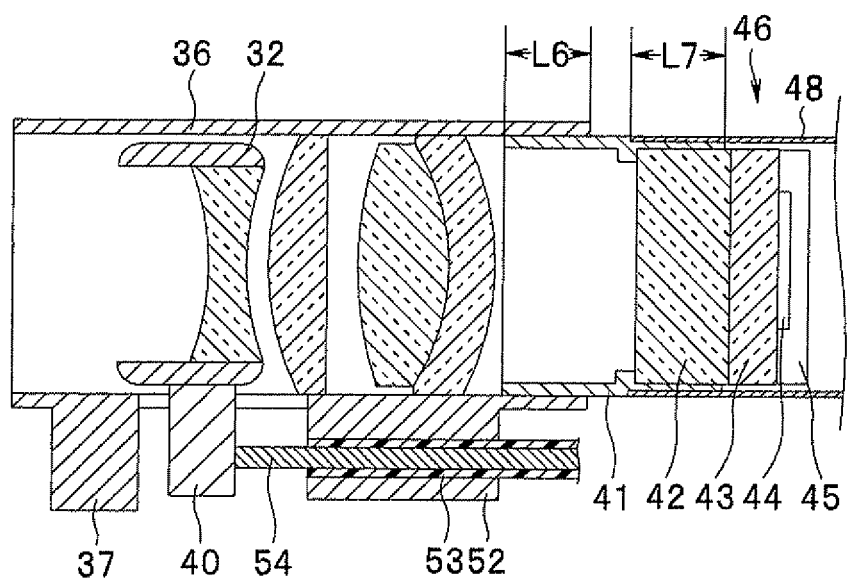
FIG. 14 is a partial sectional view showing the configuration of an image pickup apparatus equipped with a zooming/focusing optical system according to the third embodiment of the present invention.

FIG. 10 to FIG. 14 relate to the third embodiment of the present invention. FIG. 10 is a partial sectional view showing an image pickup apparatus that is fitted and fixed to a distal end rigid member. FIG. 11 is a sectional view along line XI-XI in FIG. 10. FIG. 12 is a sectional view along line XII-XII in FIG. 10. FIG. 13 is a partial sectional view showing a conventional image pickup apparatus that is fitted and fixed to a distal end rigid member that is equipped with a fixed focal length optical system. FIG. 14 is a partial sectional view showing an image pickup apparatus that is fitted and fixed to a distal end rigid member that is equipped with a zooming/focusing optical system. In the following description, the same reference numerals are used for components that are the same as components of the image pickup apparatus 30 of the endoscope 2 of the first embodiment described above, and a detailed description of those components is omitted.

The present embodiment relates to a configuration characterized by a fitting portion between an objective lens frame and a retention frame that retains a solid-state image pickup device of the image pickup apparatus. In a conventional image pickup apparatus that can perform zooming/focusing, since a retention portion that retains a drive mechanism that drives a movable lens frame extends with respect to an objective lens frame, a fitting portion between the objective lens frame and a retention frame that retains a solid-state image pickup device is fixed by fitting together the external diameter of the retention frame retaining the solid-state image pickup device and the inner diameter of the objective lens frame. According to that configuration, a fitting length between the objective lens unit and the solid-state image pickup device unit can not be adequately secured, and thus the structure is one in which the strength resistance of the image pickup apparatus is decreased. Further, it has not been possible to adequately secure a fitting length between a reinforcing frame that is disposed around the solid-state image pickup device and a retention frame that retains the solid-state image pickup device.

Therefore, as shown in FIG. 10 to FIG. 12, in the image pickup apparatus 30 of the present embodiment a notch portion 41a for avoiding the actuator retention portion 52 of the rear group lens frame 36 is formed in the solid-state image pickup device retention frame 41, and the solid-state image pickup device retention frame 41 is externally fitted onto the rear group lens frame 36.

In this state, in the solid-state image pickup device retention frame 41, a fitting length to the rear group lens frame 36 at a section at which the notch portion 41a is not formed is a predetermined length L1, and a fitting length to the rear group lens frame 36 at a section at which the notch portion 41a is formed is, for example, a predetermined length L2. Further, the reinforcing frame 48 covering the solid-state image pickup device unit 46 is externally fitted onto the solid-state image pickup device retention frame 41, and a fitting length thereof is a predetermined length L3.

In contrast, in a conventional image pickup apparatus equipped with a fixed focal length optical system, as shown in FIG. 13, the solid-state image pickup device retention frame 41 is externally fitted onto the rear group lens frame 36, and the fitting length thereof is, for example, a length L4. Further, the reinforcing frame 48 covering the solid-state image pickup device unit 46 is externally fitted onto the solid-state image pickup device retention frame 41, and the fitting length thereof is, for example, a length L5.

Further, in a conventional image pickup apparatus equipped with a zooming/focusing optical system, as shown in FIG. 14, the solid-state image pickup device retention frame 41 is internally fitted onto the rear group lens frame 36 and the fitting length thereof is, for example, a length L6. Moreover, the reinforcing frame 48 covering the solid-state image pickup device unit 46 is externally fitted onto the solid-state image pickup device retention frame 41, and the fitting length thereof is, for example, a length L7.

With respect to these conventional image pickup apparatuses, in the image pickup apparatus 30 of the present embodiment, the predetermined length L1 at which the solid-state image pickup device retention frame 41 fits onto the rear group lens frame 36 at a section at which the notch portion 41a is not formed is set to the same length as the fitting length L4 at which the solid-state image pickup device retention frame 41 of a conventional image pickup apparatus equipped with a fixed focal length optical system fits onto the rear group lens frame 36 (L1=L4).

Further, in the image pickup apparatus 30, the predetermined length L2 at which the solid-state image pickup device retention frame 41 fits onto the rear group lens frame 36 at a section at which the notch portion 41a is formed is set to the same length as the fitting length L6 at which the solid-state image pickup device retention frame 41 of a conventional image pickup apparatus equipped with a zooming/focusing optical system fits onto the rear group lens frame 36 (L2=L6).

In this connection, the relation between the fitting length L4 at which the solid-state image pickup device retention frame 41 of the conventional image pickup apparatus equipped with a fixed focal length optical system fits to the rear group lens frame 36 and the fitting length L6 at which the solid-state image pickup device retention frame 41 of a conventional image pickup apparatus equipped with a zooming/focusing optical system fits to the rear group lens frame 36 is that the fitting length L4 is longer because of the presence/absence of the actuator retention portion 52 that is a retention portion that retains a drive mechanism that drives the movable lens frame (L4>L6).

Further, in the image pickup apparatus 30 of the present embodiment, the predetermined length L3 at which the reinforcing frame 48 fits to the solid-state image pickup device retention frame 41 is set to the same length as the fitting length L5 at which the reinforcing frame 48 of a conventional image pickup apparatus equipped with a fixed focal length optical system fits to the solid-state image pickup device retention frame 41 (L3=L5).

In this connection, the relation between the fitting length L5 at which the reinforcing frame 48 of a conventional image pickup apparatus equipped with a fixed focal length optical system fits to the solid-state image pickup device retention frame 41 and the fitting length L7 at which the reinforcing frame 48 of a conventional image pickup apparatus equipped with a zooming/focusing optical system fits to the solid-state image pickup device retention frame 41 is that the fitting length L5 is longer because of the presence/absence of the actuator retention portion 52 that is a retention portion that retains a drive mechanism that drives the movable lens frame (L5>L7).

Based on the foregoing, it is found that the relationships between the fitting lengths at which the respective frames are fitted are: L1=L4>L6, L2=L6, and L3=L5>L7. Thus, in the image pickup apparatus 30 of the present embodiment, an inner diameter portion of the solid-state image pickup device retention frame 41 and an external diameter portion of the rear group lens frame 36 can be fitted together with an adequate fitting length, and adequate strength resistance can also be ensured by the solid-state image pickup device retention frame 41 that covers the entire circumference of the solid-state image pickup device chip 45.

Further, according to the image pickup apparatus 30 of the present embodiment, an inner diameter portion of the reinforcing frame 48 and an external diameter portion of the solid-state image pickup device retention frame 41 can be fitted together with an adequate fitting length, and an adequate strength resistance can also be ensured by the reinforcing frame 48 that covers the entire circumference of the solid-state image pickup device unit 46.

Fourth Embodiment

Figure 15:
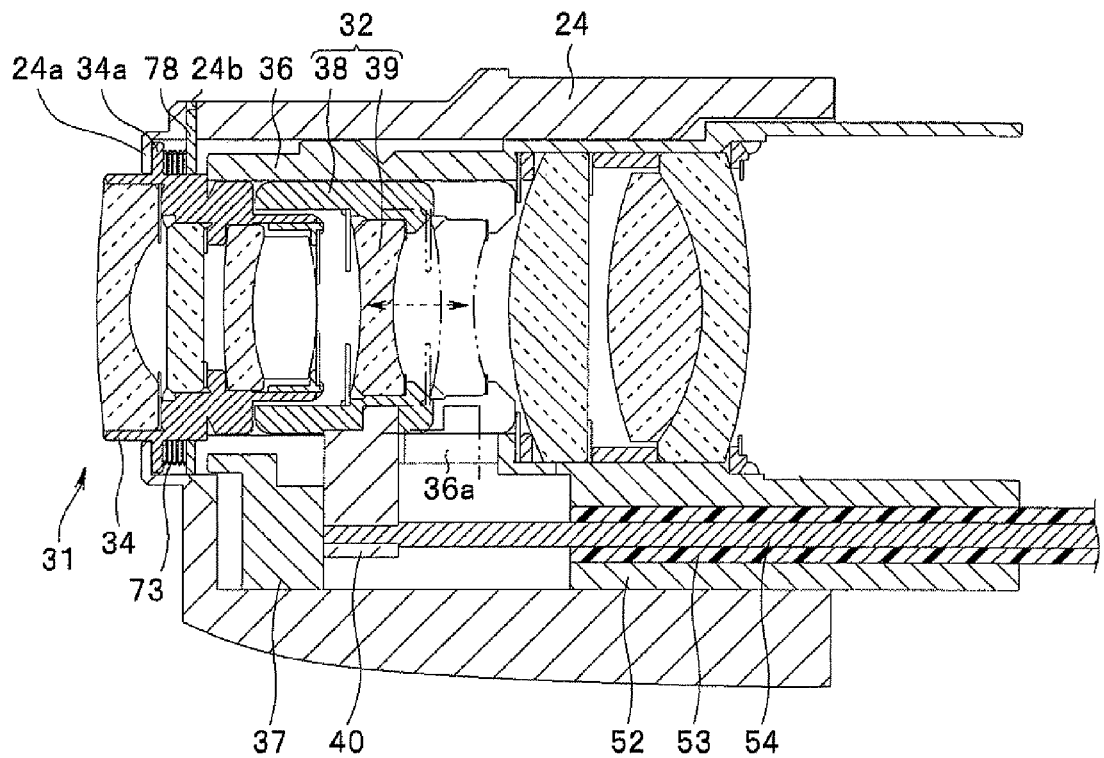
FIG. 15 is a partial sectional view showing the configuration of an image pickup apparatus that is fitted and fixed to a distal end rigid member according to a fourth embodiment of the present invention.
Figure 16:
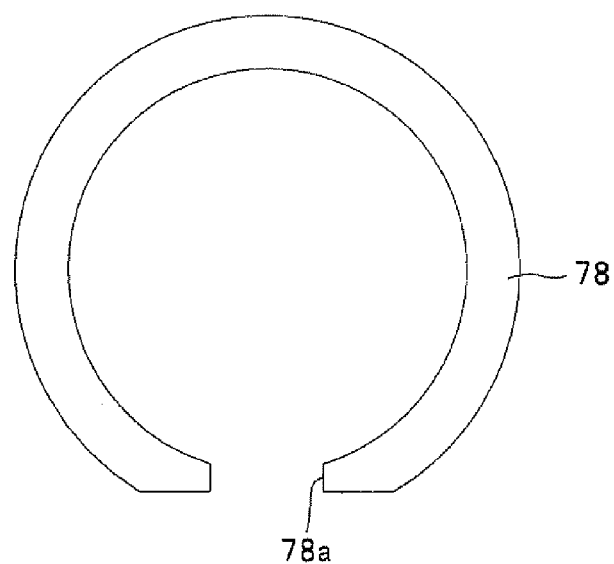
FIG. 16 is a view showing the configuration of a stopper ring according to the fourth embodiment of the present invention.

Next, the fourth embodiment of the present invention is described based on FIG. 15 and FIG. 16.

FIG. 15 and FIG. 16 relate to the fourth embodiment of the present invention. FIG. 15 is a partial sectional view showing an image pickup apparatus that is fitted and fixed to a distal end rigid member. FIG. 16 is a view showing the configuration of a stopper ring. In the following description, the same reference numerals are used for components that are the same as components of the image pickup apparatus 30 of the endoscope 2 of the first embodiment described above, and a detailed description of those components is omitted.

The present embodiment relates to a configuration characterized by having retention means that retains an image pickup apparatus at a distal end rigid member of an endoscope. Conventionally, when fixing an image pickup apparatus equipped with a movable lens unit to a distal end rigid member of an endoscope, assembly is carried out by screwing a fixing screw against a groove portion formed on the outer circumference of a lens frame within which a movable lens unit moves forward and backward. However, in some cases screwing the fixing screw against the groove portion causes the lens frame to change shape, increases frictional resistance between the inner surface thereof and the outer circumferential surface of the movable lens unit, and hinders the movable lens unit from sliding smoothly. This has been a cause of a sliding failure.

Therefore, as shown in FIG. 15 and FIG. 16, the image pickup apparatus 30 of the present embodiment is configured to be fixed to a distal end rigid member 24 via a front group lens frame 34 by a stopper ring 78 and a spring 73, to thus prevent a sliding failure and enable the movable lens unit to slide smoothly.

More specifically, as shown in FIG. 15, a spring 73 is externally fitted onto the front group lens frame 34 so as to abut against an outward flange 34a provided at the outer circumference of the distal end portion. The outward flange 34a contacts against an inward flange 24a formed at the distal end of the distal end rigid member 24.

As shown in FIG. 16, in the distal end rigid member 24, a slit portion 24b in which a thin, tabular stopper ring 78 is provided in an inserted manner is formed along the outer circumference of the distal end portion. A notch 78a is formed at one section of the stopper ring 78 so as to expand in the outer circumferential direction.

After the image pickup apparatus 30 is insertedly arranged in the distal end rigid member 24, the stopper ring 78 is expanded in the outer circumferential direction in the slit portion 24b to be fitted to the outer circumferential portion of the front group lens frame 34. At this time, the spring 73 abuts against one face of the stopper ring 78, the outward flange 34a of the front group lens frame 34 is pressed by the urging force of the spring 73, and the outward flange 34a is brought in abutment with the inward flange 24a of the distal end rigid member 24. In this manner, the image pickup apparatus 30 is fixed to the distal end rigid member 24.

Thus, the image pickup apparatus 30 of the present embodiment has a configuration that does not cause a sliding failure due to, for example, the inner diameter of the rear group lens frame 36 in which the movable lens unit 32 moves forward and backward narrowing due to a change in shape of the rear group lens frame 36 caused by a fixing screw that fixes the image pickup apparatus 30 to the distal end rigid member 24, and consequently an obstruction to the forward and backward movement of the movable lens unit 32 is prevented. As a result, the sliding performance with which the movable lens unit 32 moves forward and backward smoothly inside the rear group lens frame 36 is enhanced.

Fifth Embodiment

Next, the fifth embodiment of the present invention is described based on FIG. 17 to FIG. 20.

Figure 17:
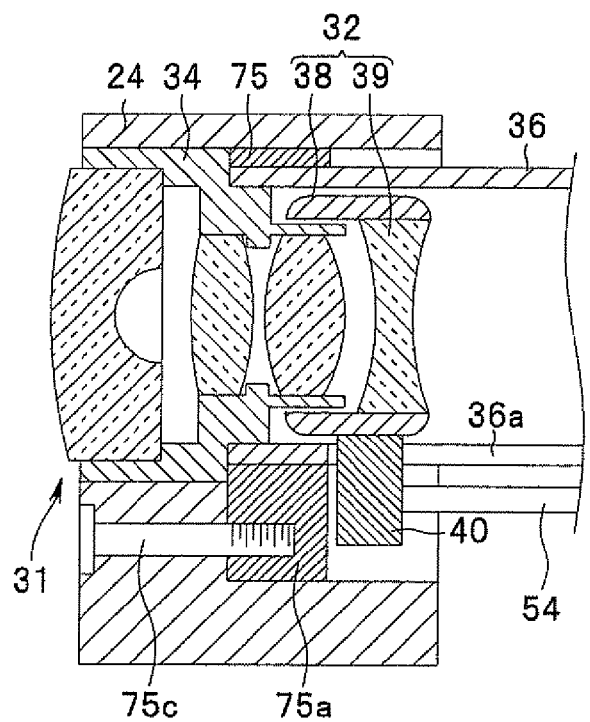
FIG. 17 is a partial sectional view showing the configuration of an image pickup apparatus that is fitted and fixed to a distal end rigid member according to a fifth embodiment of the present invention.
Figure 18:
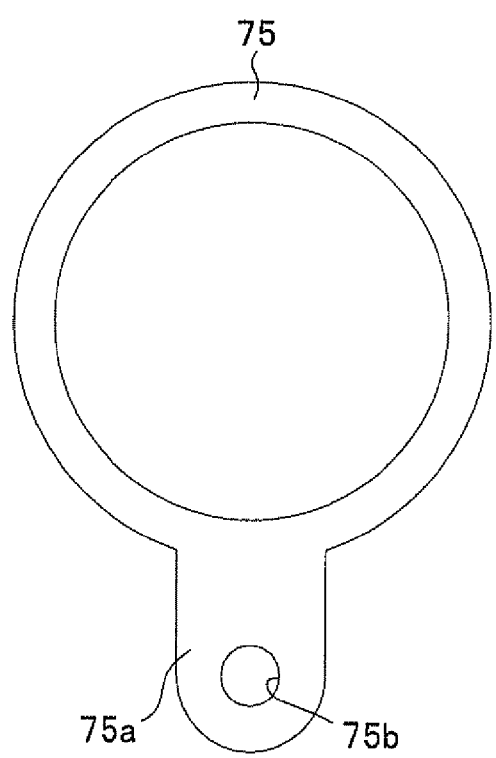
FIG. 18 is a view showing the configuration of a frame retainer according to the fifth embodiment of the present invention.
Figure 19:
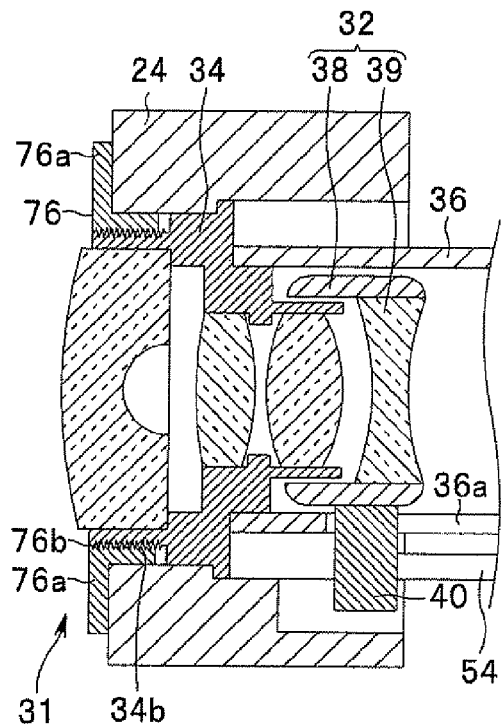
FIG. 19 is a partial sectional view showing the configuration of an image pickup apparatus that is fitted and fixed to a distal end rigid member according to a first modification example of the fifth embodiment of the present invention.
Figure 20:
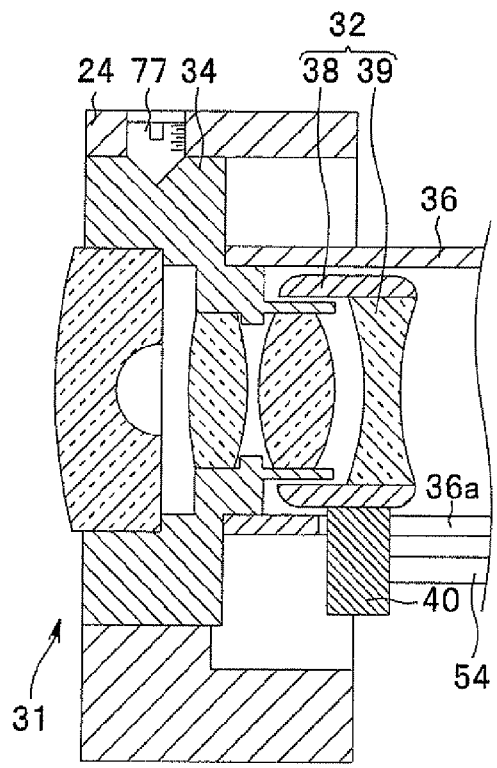
FIG. 20 is a partial sectional view showing the configuration of an image pickup apparatus that is fitted and fixed to a distal end rigid member according to a second modification example of the fifth embodiment of the present invention.

FIG. 17 to FIG. 20 relate to the fifth embodiment of the present invention. FIG. 17 is a partial sectional view showing an image pickup apparatus that is fitted and fixed to a distal end rigid member. FIG. 18 is a view showing the configuration of a frame retainer. FIG. 19 is a partial sectional view showing an image pickup apparatus that is fitted and fixed to a distal end rigid member according to a first modification example. FIG. 20 is a partial sectional view showing an image pickup apparatus that is fitted and fixed to a distal end rigid member according to a second modification example. In the following description, the same reference numerals are used for components that are the same as components of the image pickup apparatus 30 of the endoscope 2 of the first embodiment described above, and a detailed description of those components is omitted.

Similarly to the fourth embodiment, the present embodiment is a configuration example for preventing a sliding failure so that a movable lens unit of the image pickup apparatus 30 can slide smoothly.

According to the present embodiment, as shown in FIG. 17, a circumferential surface formed at the rear of the front group lens frame 34 is abutted against from the rear by a frame retainer 75, and the frame retainer 75 and a distal end rigid member 24 are fixed by a screw 75c from the front surface direction to thereby fix the image pickup apparatus 30 to the distal end rigid member 24.

As shown in FIG. 18, the frame retainer 75 includes a contact portion 75a that includes a screw hole 75b into which the screw 75c is screwed that extends from a ring-shaped outer circumferential portion. When the screw 75c is tightened, as shown in FIG. 17, the contact portion 75a is drawn forward to be brought in contract with one surface at the rear of the front group lens frame 34 and the back face of the distal end rigid member 24.

Thus, similarly to the fourth embodiment, the image pickup apparatus 30 of the present embodiment has a configuration that does not cause a sliding failure due to, for example, the inner diameter of the rear group lens frame 36 in which the movable lens unit 32 moves forward and backward narrowing due to a change in the shape of the rear group lens frame 36 caused by a fixing screw that fixes the image pickup apparatus 30 to the distal end rigid member 24. Thus, an obstruction to the forward and backward movement of the movable lens unit 32 is prevented. As a result, the sliding performance with which the movable lens unit 32 moves forward and backward smoothly inside the rear group lens frame 36 is enhanced.

Moreover, since the image pickup apparatus 30 is fixed from the front, interference of screws that fix other internal components or the like can be prevented, and a reduction in the diameter of the distal end portion 12 of the endoscope 2 and a shortening of the rigid portion length can be realized. Further, the configuration of the image pickup apparatus 30 is such that assembly to and detachment from the distal end rigid member 24 can be easily performed.

In this connection, as shown in FIG. 19, the front group lens frame 34 of the image pickup apparatus 30 may also be fixed to the distal end rigid member 24 by a substantially ring-shaped fixing member 76 that includes an outward flange 76a.

More specifically, at the inner circumferential surface, the fixing member 76 includes a screw portion 76b that is screwed with a screw portion 34b formed at the outer circumferential portion of the distal end of the front group lens frame 34. The fixing member 76 is a member that fixes the image pickup apparatus 30 to the distal end rigid member 24 by contacting against the distal end face of the distal end rigid member 24 by means of the outward flange 76a so as to sandwich the distal end rigid member 24 between the outward flange 76a and the front group lens frame 34.

Further, as shown in FIG. 20, a distal end outer circumferential portion of the front group lens frame 34 at which the movable lens unit 32 does not move forward or rearward may be fixed to the distal end rigid member 24 by a screw 77.

Sixth Embodiment

Next, the sixth embodiment of the present invention is described based on FIG. 21 to FIG. 24.

Figure 21:
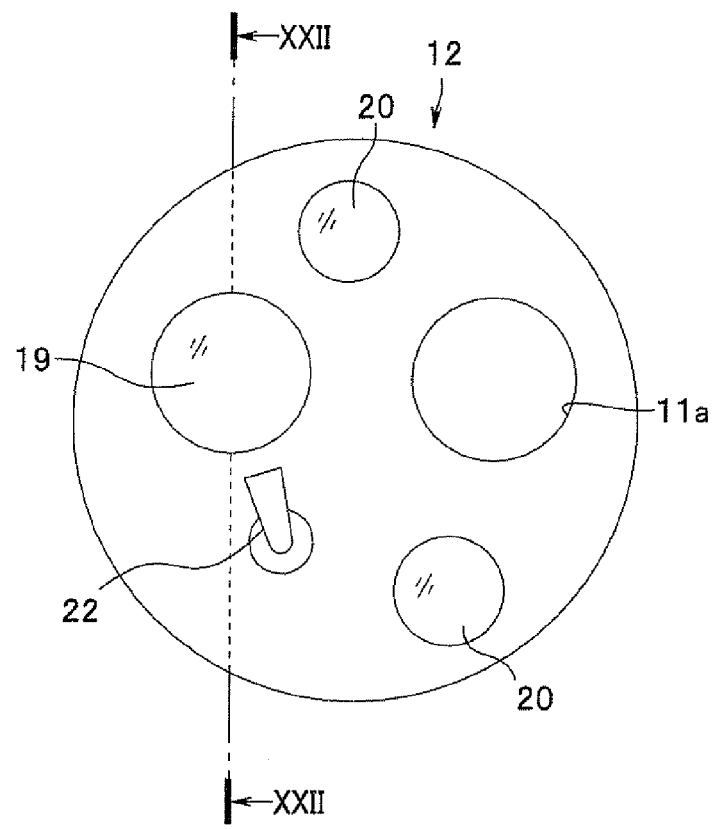
FIG. 21 is a view of a distal end portion of an insertion portion of an endoscope according to a sixth embodiment as viewed from the front.
Figure 22:
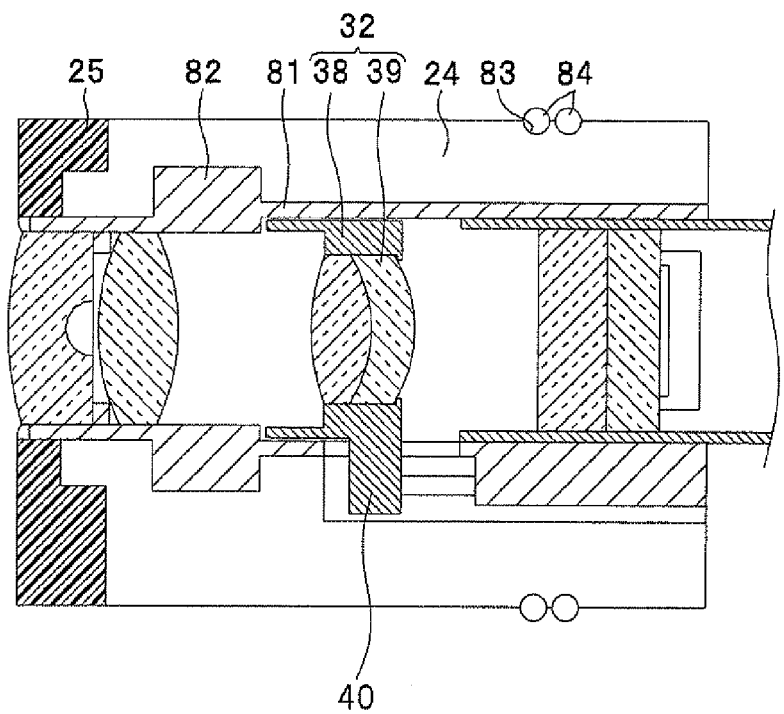
FIG. 22 is a sectional view of the distal end portion according to the sixth embodiment that is taken along line XXII-XXII in FIG. 21.
Figure 23:
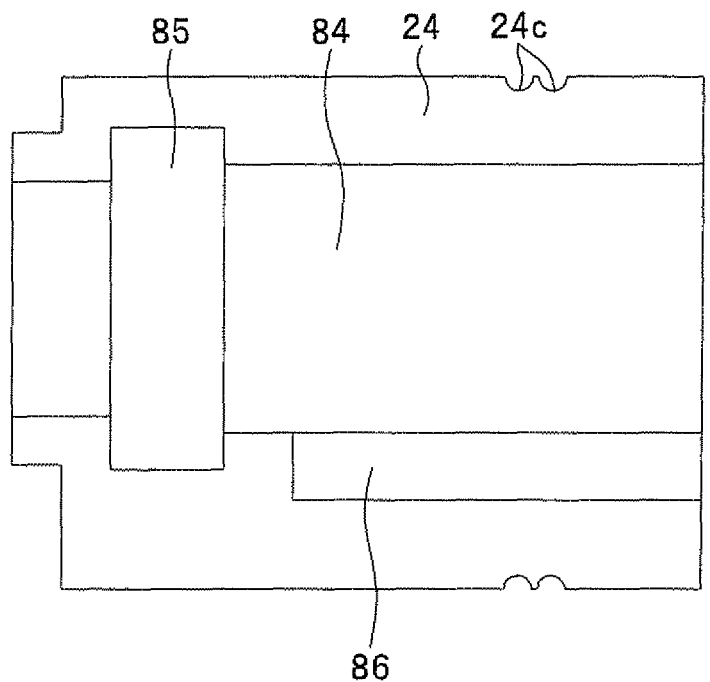
FIG. 23 is a view showing the configuration of a divided distal end rigid member according to the sixth embodiment.
Figure 24:
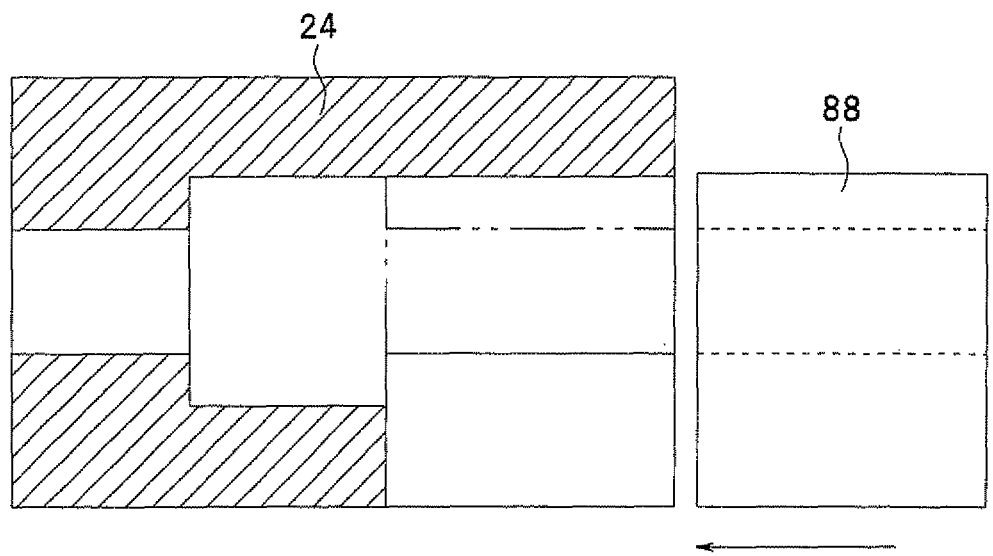
FIG. 24 is a view showing the configuration of a distal end rigid member according to a modification example of the sixth embodiment.

FIG. 21 to FIG. 24 relate to the sixth embodiment of the present invention. FIG. 21 is a view of a distal end portion of an insertion portion of an endoscope as viewed from the front. FIG. 22 is a sectional view taken along line XXII-XXII in FIG. 21. FIG. 23 is a view showing the configuration of a distal end rigid member that is divided. FIG. 24 is a view showing the configuration of a distal end rigid member according to a modification example. In the following description, the same reference numerals are used for components that are the same as components of the image pickup apparatus 30 of the endoscope 2 of the first embodiment described above, and a detailed description of those components is omitted.

The present embodiment is a configuration example for preventing a sliding failure so that a movable lens unit of the image pickup apparatus 30 can slide smoothly, similarly to the fourth and fifth embodiments.

In some cases, a conventional image pickup apparatus is fixed with adhesive to a distal end rigid member. When an image pickup apparatus is fixed with an adhesive in this manner, it is necessary for other internal components such as a nozzle, a channel, and a light guide to be integrally fixed with adhesive also.

In such case, it is difficult to remove the image pickup apparatus at the time of maintenance. Further, when performing maintenance individually on the respective internal components, it is not possible to replace the components with individual replacement parts because of the filled adhesive. Consequently, this kind of configuration leads to waste.

Therefore, as shown in FIG. 21 to FIG. 23, the image pickup apparatus 30 according to the present embodiment has a configuration in which the distal end rigid member 24 is divided to retain and fix the image pickup apparatus 30.

More specifically, the distal end rigid member 24 has a configuration that is divided in two along line XII-XII shown in FIG. 21. The divided distal end rigid member 24 is bound with thread 83 at a spool groove 24c to fix together the two parts of the divided member. These divided parts of the distal end rigid member 24 are divided at a face that includes the photographing optical axis of the objective lens of the image pickup apparatus 30.

As shown in FIG. 23, a groove 84 that fits and fixes the image pickup apparatus 30 is formed in each of the parts of the distal end rigid member 24 that is divided in two. Further, an insertion groove 85 into which a flange portion 82 of the fixed lens frame 81 of the image pickup apparatus 30 is engageably inserted is formed in each of these parts of the distal end rigid member 24.

By inserting the flange portion 82 into the insertion groove 85, movement in the optical axis direction of the image pickup apparatus 30 that is fittingly retained by the distal end rigid member 24 is regulated. In this connection, grooves in which internal components such as an unshown illumination lens unit, treatment instrument channel, nozzle and the like are fitted and fixed are provided in the distal end rigid member 24.

According to such a configuration like this, similarly to the fourth and fifth embodiments, the image pickup apparatus 30 of the present embodiment has a configuration that does not cause a sliding failure due to, for example, the inner diameter of the rear group lens frame 36 in which the movable lens unit 32 moves forward and backward narrowing due to a change in shape of the rear group lens frame 36 caused by a fixing screw that fixes the image pickup apparatus 30 to the distal end rigid member 24, and thus obstruction of forward and backward movement of the movable lens unit 32 is prevented. As a result, the sliding performance with which the movable lens unit 32 moves forward and backward smoothly inside the rear group lens frame 36 is enhanced.

Further, since the distal end rigid member 24 that includes two parts is joined together by binding with thread 83, the individual parts can be fitted and fixed with almost no increase in the external diameter thereof. Moreover, the configuration thereof is such that internal components can be easily removed at the time of maintenance by untying the bound thread 83.

In this connection, as shown in FIG. 24, a configuration may also be adopted in which the dividing position (dividing surface) of the distal end rigid member 24 is different to the above configuration. FIG. 24 shows a configuration in which a part 88 that fits in the lateral direction from a side circumferential portion on the rearward side of the distal end rigid member 24 is fitted and fixed after an internal component such as the image pickup apparatus 30 is installed.

By adopting such a configuration like this, the distal end rigid member 24 easily maintains watertightness since the dividing surface is not on the distal end face side.

Seventh Embodiment

Next, the seventh embodiment of the present invention is described below based on FIG. 25 and FIG. 26.

Figure 25:
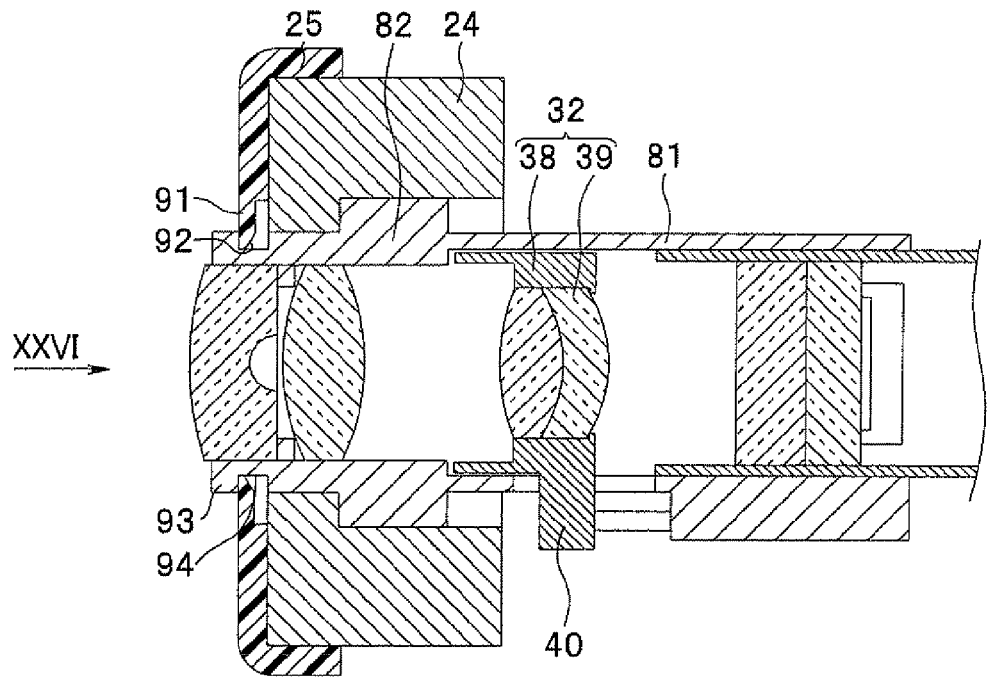
FIG. 25 is a partial sectional view showing the configuration of an image pickup apparatus that is fitted and fixed to a distal end rigid member according to a seventh embodiment of the present invention.
Figure 26:
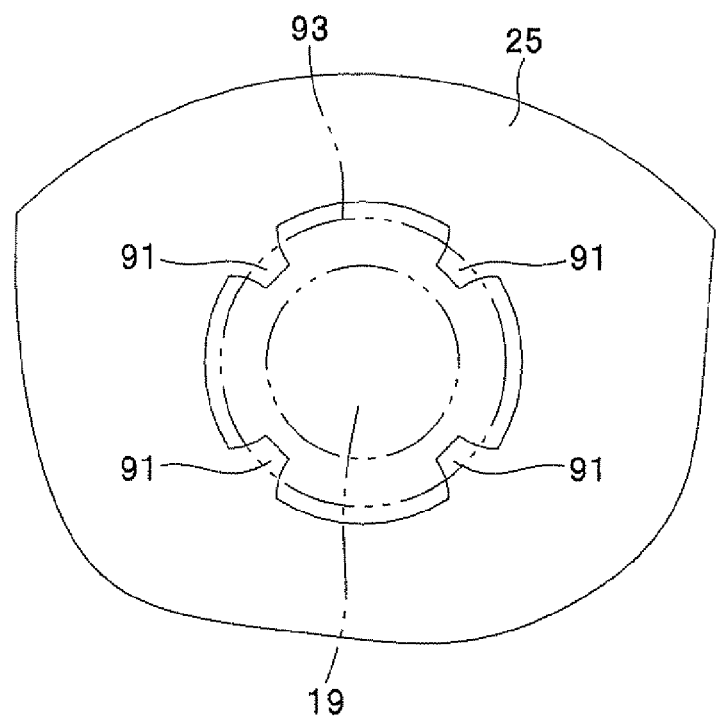
FIG. 26 is a view from the direction of arrow XXVI in FIG. 25 according to the seventh embodiment of the present invention.

FIG. 25 and FIG. 26 relate to the seventh embodiment of the present invention. FIG. 25 is a partial sectional view showing an image pickup apparatus that is fitted and fixed to a distal end rigid member. FIG. 26 is a view from the direction of arrow XXVI in FIG. 25. In the following description, the same reference numerals are used for components that are the same as in the image pickup apparatus 30 of the endoscope 2 of the first and sixth embodiments described above, and a detailed description of those components is omitted.

The present embodiment is a configuration example for preventing a sliding failure so that a movable lens unit of the image pickup apparatus 30 can slide smoothly, similarly to the fourth to sixth embodiments.

As shown in FIG. 25, the image pickup apparatus 30 of the present embodiment is mounted in a state in which the image pickup apparatus 30 is held between the flange portion 82 of the fixed lens frame 81 and the distal end cover 25, and is retained by the distal end rigid member 24.

More specifically, as shown in FIG. 26, a hole portion for the image pickup apparatus 30 of the distal end cover 25 has a plurality of claw-shaped protruding portions 91 that are arranged to extend towards the hole center. In this case four protruding portions 91 are provided. Further, a tapered portion 92 that inclines towards the protruding end on the rear face side is formed in the protruding portions 91.

First, the flange portion 82 is abutted against the distal end rigid member 24 to fit the image pickup apparatus 30. The distal end cover 25 is then mounted from the front of the distal end rigid member 24. At this time, the four protruding portions 91 provided in the distal end cover 25 enter a circumferential groove 94 provided on the outer circumference of the distal end lens retention portion 93 of the fixed lens frame 81. Since tapered portion 92 is formed on the rear face side of each protruding portion 91, the distal end lens retention portion 93 can be passed over easily.

Thus, the image pickup apparatus 30 of the present embodiment is fitted and fixed in the distal end rigid member 24 by the flange portion 82 abutting against the distal end rigid member 24 and the protruding portions 91 of the distal end cover 25 entering the circumferential groove 94 of the fixed lens frame 81.

According to such a configuration like this, similarly to the fourth to sixth embodiments, the image pickup apparatus 30 of the present embodiment has a configuration that does not cause a sliding failure due to, for example, the inner diameter of the rear group lens frame 36 in which the movable lens unit 32 moves forward and backward narrowing due to a change in shape of the rear group lens frame 36 caused by a fixing screw that fixes the image pickup apparatus 30 to the distal end rigid member 24, and thus obstruction of forward and backward movement of the movable lens unit 32 is prevented. As a result, the sliding performance with which the movable lens unit 32 moves forward and backward smoothly inside the rear group lens frame 36 is enhanced. Furthermore, not only can assembly of the image pickup apparatus 30 to the distal end rigid member 24 be completed by simply fitting on the distal end cover 25, but the image pickup apparatus 30 can also be taken out easily when performing maintenance by merely trimming off the four protruding portions 91 of the distal end cover 25.

Eighth Embodiment

Next, the eighth embodiment of the present invention is described below based on FIG. 27 and FIG. 28.

Figure 27:
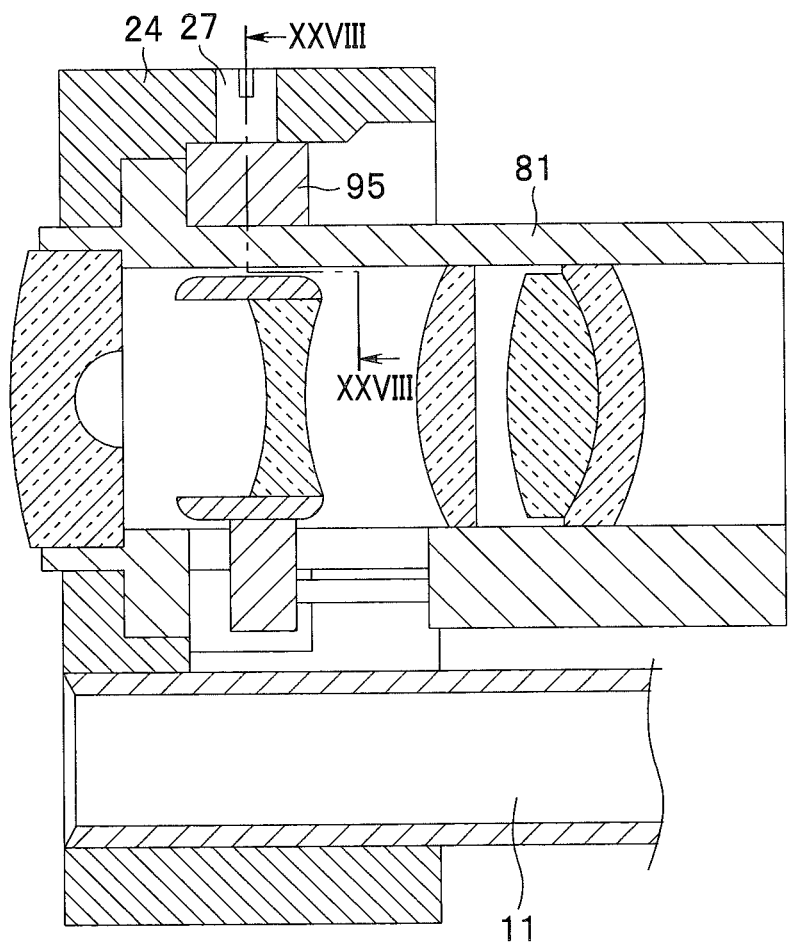
FIG. 27 is a partial sectional view showing an image pickup apparatus that is fitted and fixed to a distal end rigid member according to an eighth embodiment of the present invention.
Figure 28:
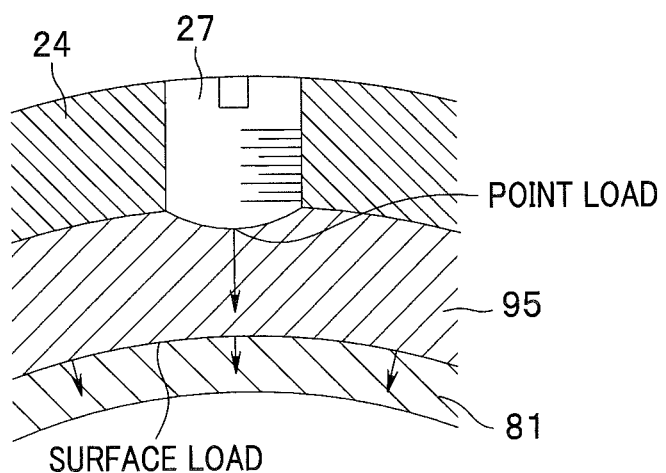
FIG. 28 is a sectional view according to the eighth embodiment of the present invention along line XXVIII-XXVIII in FIG. 27.
Figure 29:
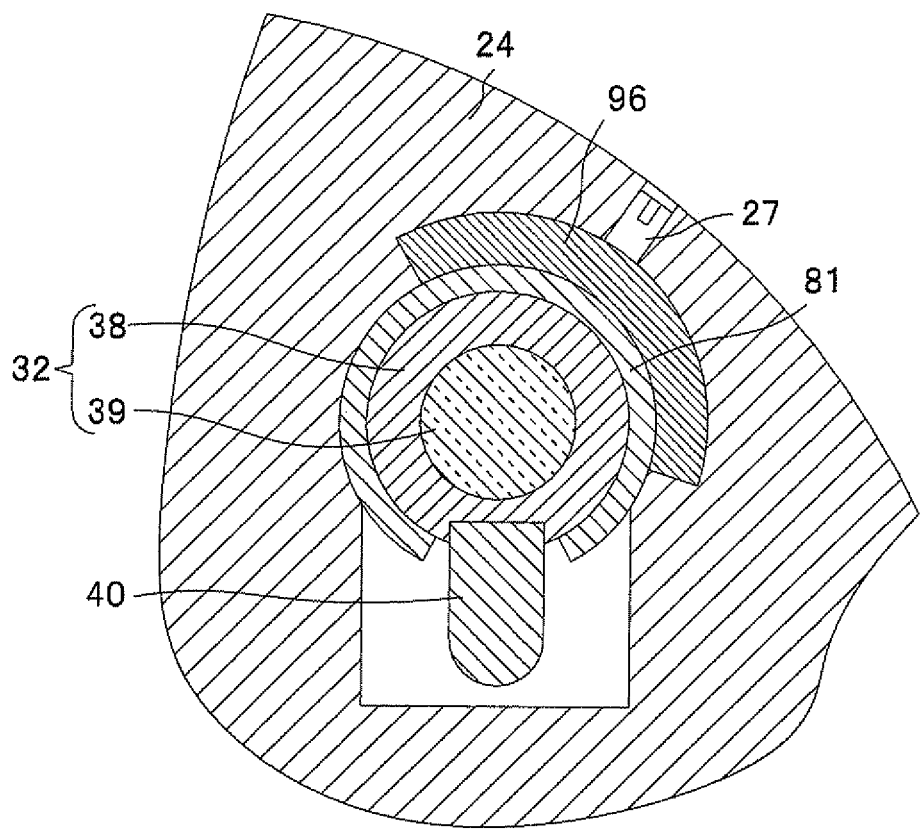
FIG. 29 is a partial sectional view showing an image pickup apparatus that is fitted and fixed to a distal end rigid member according to a modification example of the eighth embodiment.

FIG. 27 to FIG. 29 relate to the eighth embodiment of the present invention. FIG. 27 is a partial sectional view showing an image pickup apparatus that is fitted and fixed to a distal end rigid member. FIG. 28 is a sectional view along line XXVIII-XXVIII in FIG. 27. FIG. 29 is a partial sectional view showing an image pickup apparatus that is fitted and fixed to a distal end rigid member according to a modification example. In the following description, the same reference numerals are used for components that are the same as in the image pickup apparatus 30 of the endoscope 2 of the first and sixth embodiments described above, and a detailed description of those components is omitted.

The present embodiment is a configuration example for preventing a sliding failure so that a movable lens unit of the image pickup apparatus 30 can slide smoothly even when using a set screw.

As shown in FIG. 27 and FIG. 28, a fixing ring 95 is provided around the circumference of the fixed lens frame 81 so that the set screw 27 that fixes the fixed lens frame 81 of the image pickup apparatus 30 to the distal end rigid member 24 presses the fixed lens frame 81 with a surface load. The fixing ring 95 is formed with a material that has a smaller degree of elasticity than the fixed lens frame 81, for example, aluminum, brass, or a rubber material.

Thus, according to the present embodiment, by providing the fixing ring 95 that changes a point load from the set screw 27 into a surface load, a change in shape of the lens frame can be suppressed.

Thus, similarly to the fourth to seventh embodiments, the image pickup apparatus 30 of the present embodiment also has a configuration that does not cause a sliding failure due to, for example, the inner diameter of the rear group lens frame 36 in which the movable lens unit 32 moves forward and backward narrowing due to a change in shape of the rear group lens frame 36 caused by a fixing screw that fixes the image pickup apparatus 30 to the distal end rigid member 24, and thus obstruction of forward and backward movement of the movable lens unit 32 is prevented. As a result, the sliding performance with which the movable lens unit 32 moves forward and backward smoothly inside the rear group lens frame 36 is enhanced.

In this connection, a fixing ring that pressingly fixes the fixed lens frame 81 with a surface load is not limited to a circular ring shape. For example, as shown in FIG. 29, the fixing ring may be a fixing member 96 that has a substantially semicircular-shaped cross section along the outer circumferential surface of the fixed lens frame 81.

Ninth Embodiment

Figure 30:
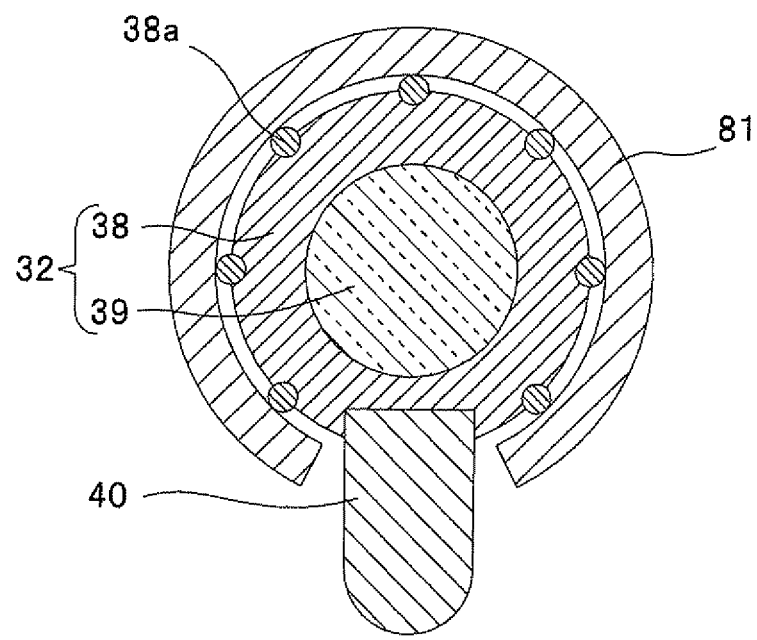
FIG. 30 is a sectional view showing a movable lens unit that is disposed inside a fixed lens frame 81 according to a ninth embodiment.
Figure 33:
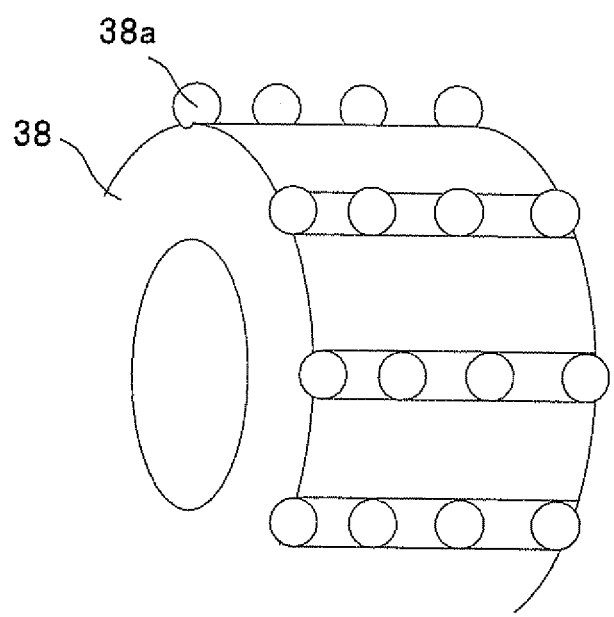
FIG. 33 is an oblique perspective view showing an example of a movable lens frame that is different to the examples shown in FIG. 31 and FIG. 32 according to the ninth embodiment.

Next, the ninth embodiment of the present invention is described based on FIG. 30 and FIG. 33.

Figure 31:
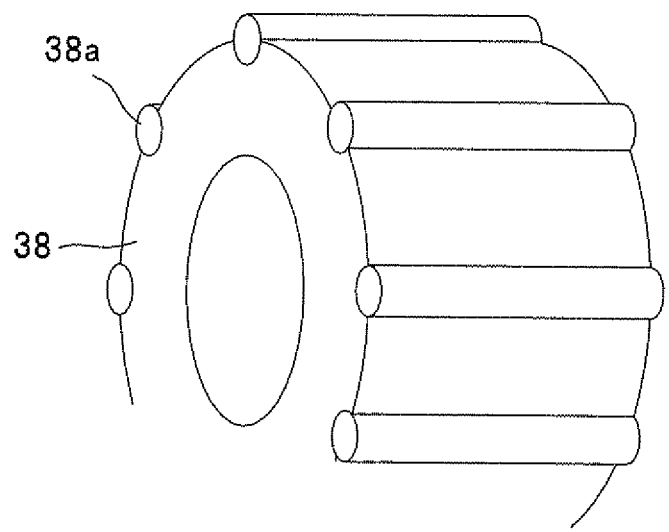
FIG. 31 is an oblique perspective view showing an example of the movable lens frame shown in FIG. 30 according to the ninth embodiment.
Figure 32:
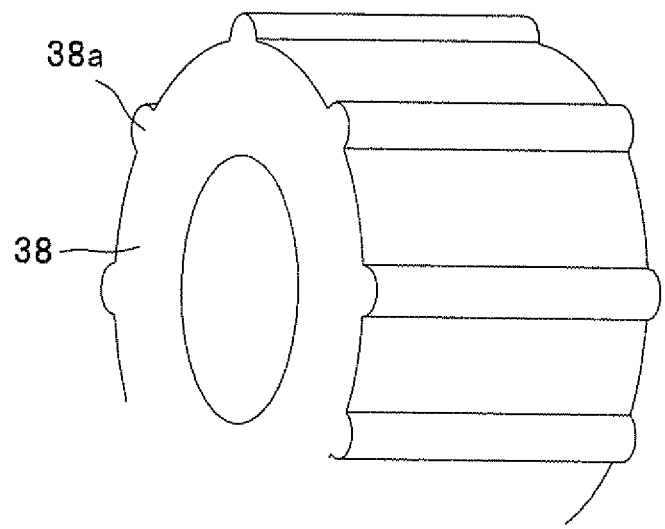
FIG. 32 is an oblique perspective view showing an example of a movable lens frame that is different to the example shown in FIG. 31 according to the ninth embodiment.

FIG. 30 to FIG. 33 relate to the ninth embodiment of the present invention. FIG. 30 is a sectional view showing a movable lens unit that is disposed inside the fixed lens frame 81. FIG. 31 is an oblique perspective view showing an example of a movable lens frame. FIG. 32 is an oblique perspective view showing an example of a movable lens frame that is different to the example shown in FIG. 31. FIG. 33 is an oblique perspective view showing an example of a movable lens frame that is different to the examples shown in FIG. 31 and FIG. 32. In the following description, the same reference numerals are used for components that are the same as in the image pickup apparatus 30 of the endoscope 2 of the first and sixth embodiments described above, and a detailed description of those components is omitted.

The present embodiment is an example that is configured so that a movable lens unit inside a lens frame can move forward and backward smoothly.

As shown in FIG. 30, the movable lens frame 38 of the movable lens unit 32 of the present embodiment has a configuration in which the area that contacts with an inner surface of the fixed lens frame 81 along the outer circumferential surface of the movable lens frame 38 is decreased, and a plurality of contact-reducing portions 38a for reducing frictional resistance are provided at substantially regular intervals around the circumference thereof.

The contact-reducing portions 38a may be formed in a rod shape as shown in FIG. 31 and configured to contact by line contact with the inner surface of the fixed lens frame 81, or may be configured so as to integrally protrude in a semi-circular shape from the outer circumferential surface of the movable lens frame 38 as shown in FIG. 32, or may be formed as a plurality of spheres that are arranged in a row as shown in FIG. 33 so as to contact by point contact with the inner surface of the fixed lens frame 81.

By providing the contact-reducing portions 38a in the movable lens frame 38 in this manner, since the sliding resistance with respect to the fixed lens frame 81 is reduced, the movable lens unit 32 can move forward and backward smoothly within the fixed lens frame 81.

Tenth Embodiment

Next, the tenth embodiment of the present invention is described below based on FIG. 34 to FIG. 39.

Figure 34:
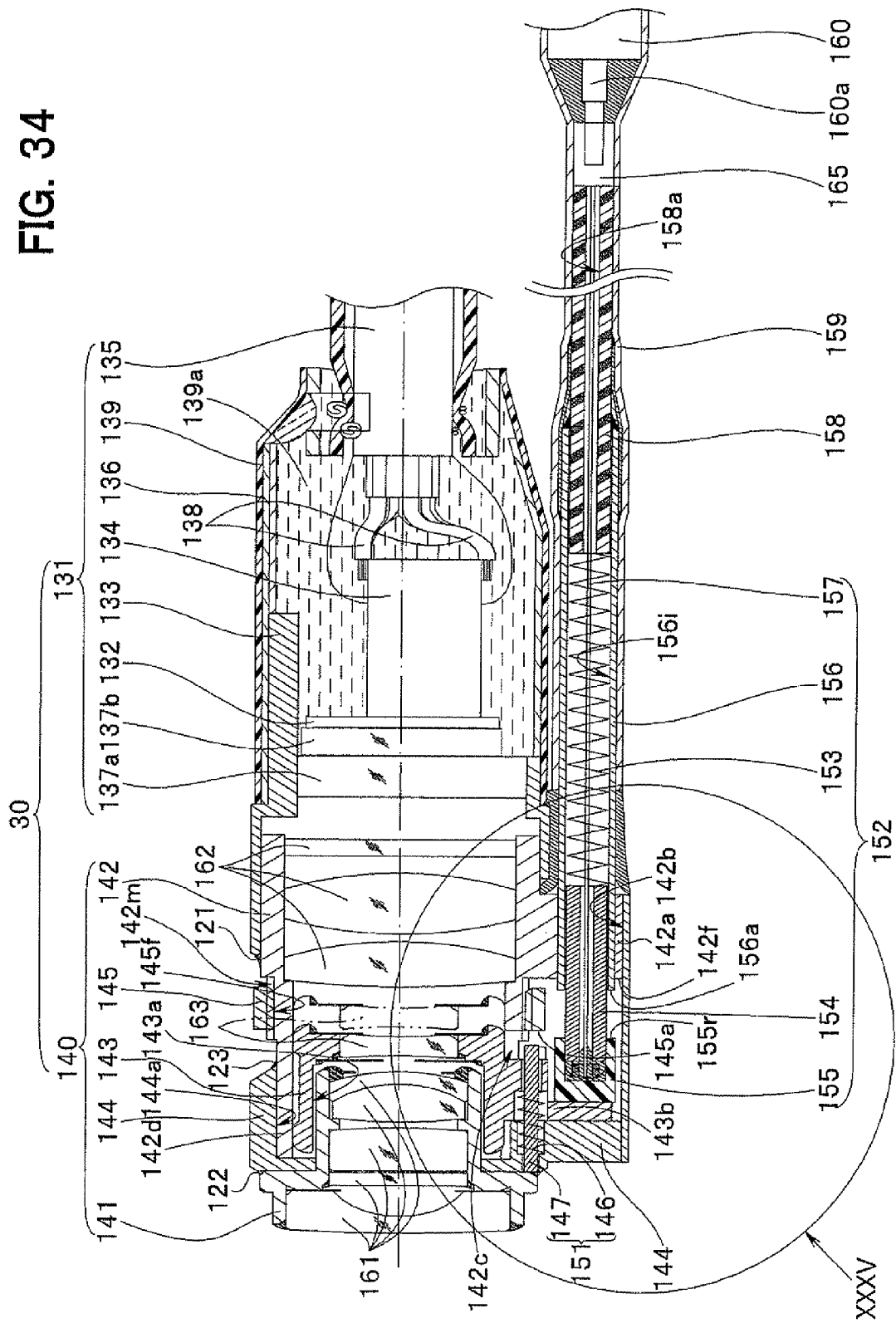
FIG. 34 is a view that describes the configuration of an image pickup unit according to a tenth embodiment.
Figure 35:
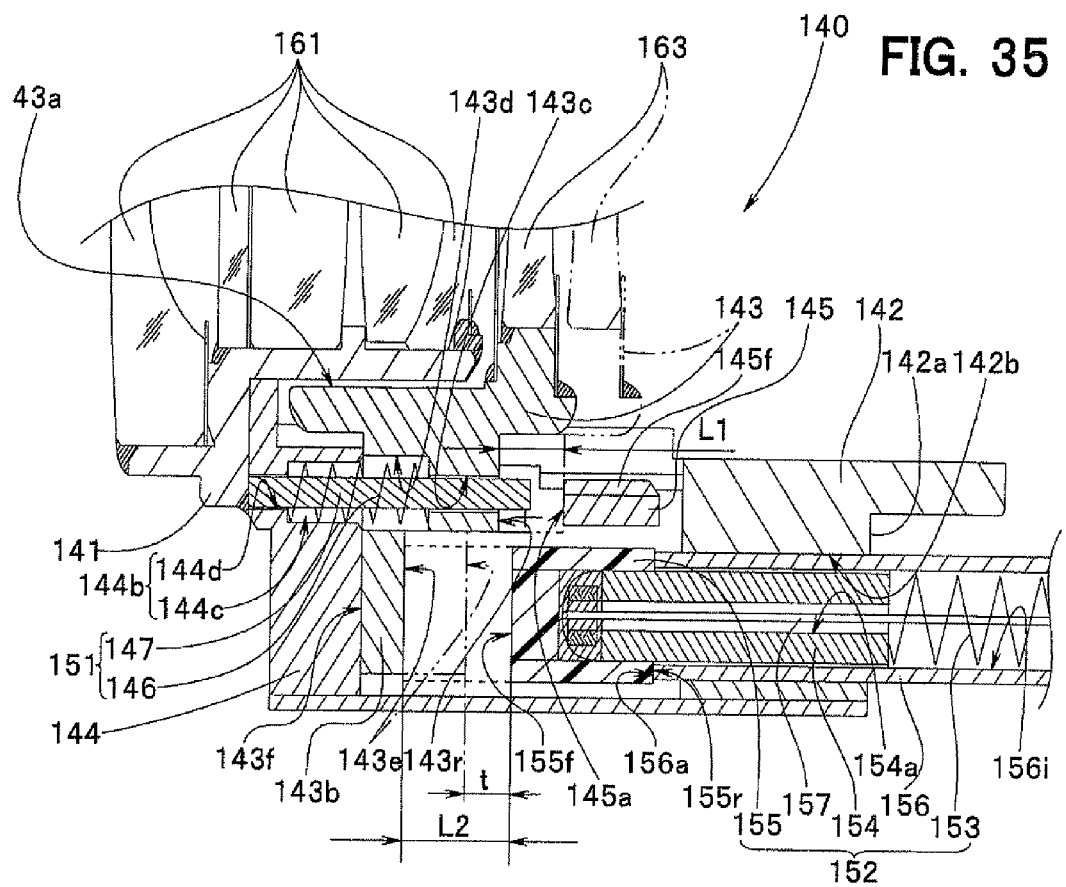
FIG. 35 is an enlarged view of a part indicated by arrow XXXV in FIG. 34 according to the tenth embodiment.
Figure 36:
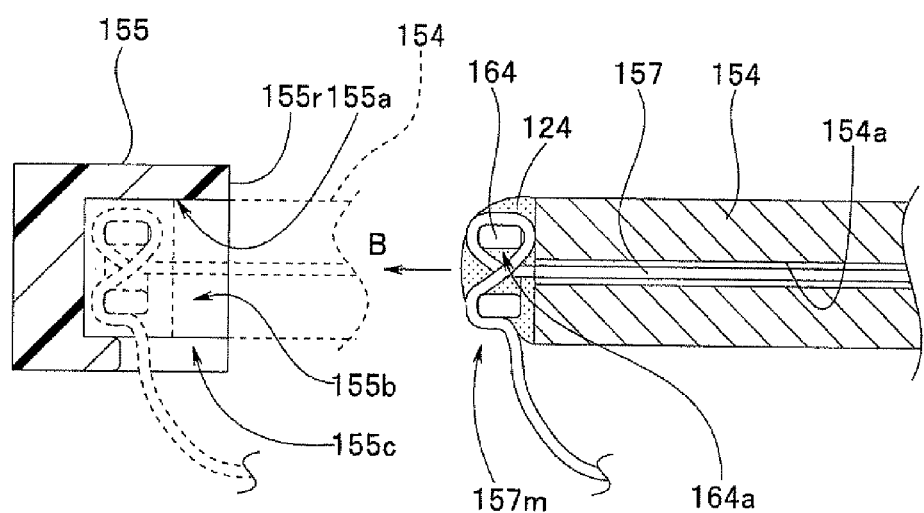
FIG. 36 is a view that illustrates a process of fixedly installing a ring member in which an SMA wire is fixed to a contact member according to the tenth embodiment.
Figure 37:
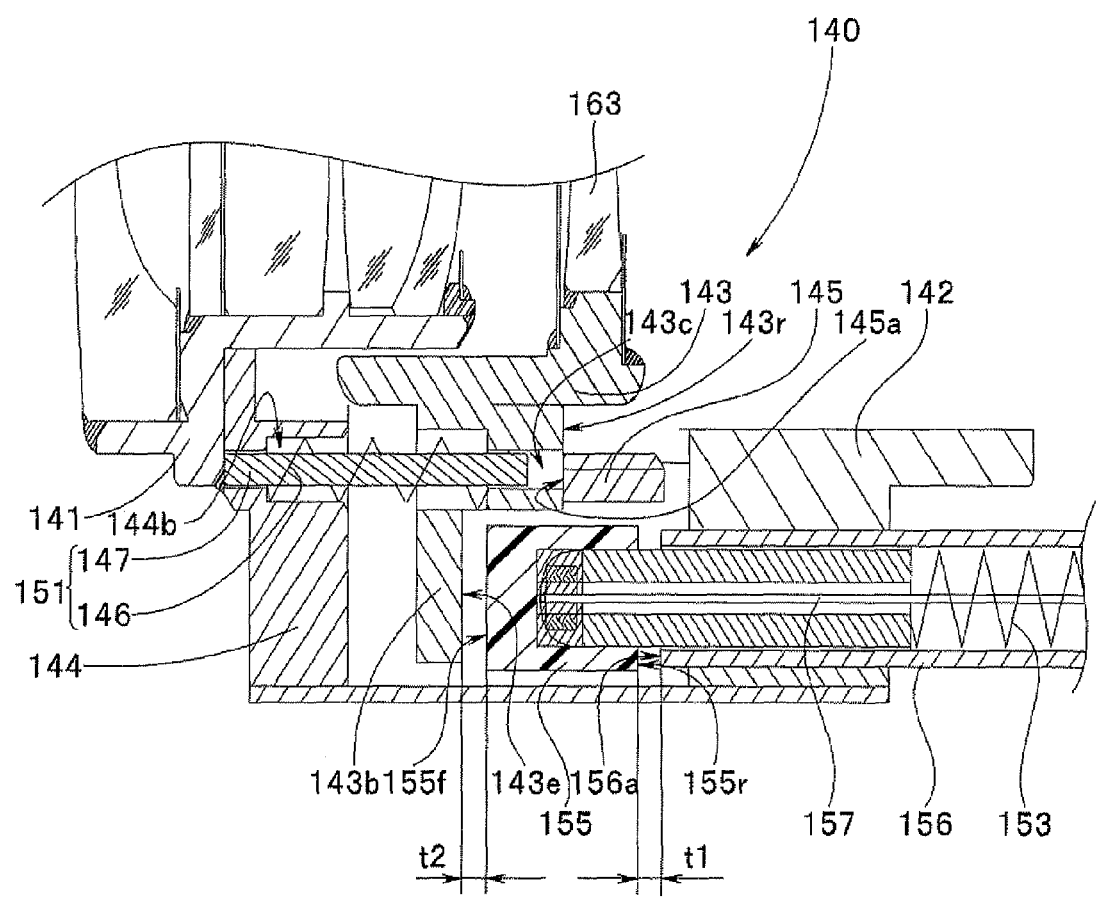
FIG. 37 is a view that illustrates the positional relationship between a contact member and a guide pipe and the positional relationship between the contact member and a movable lens frame when the contact member is disposed at an overheat prevention position according to the tenth embodiment.
Figure 38:
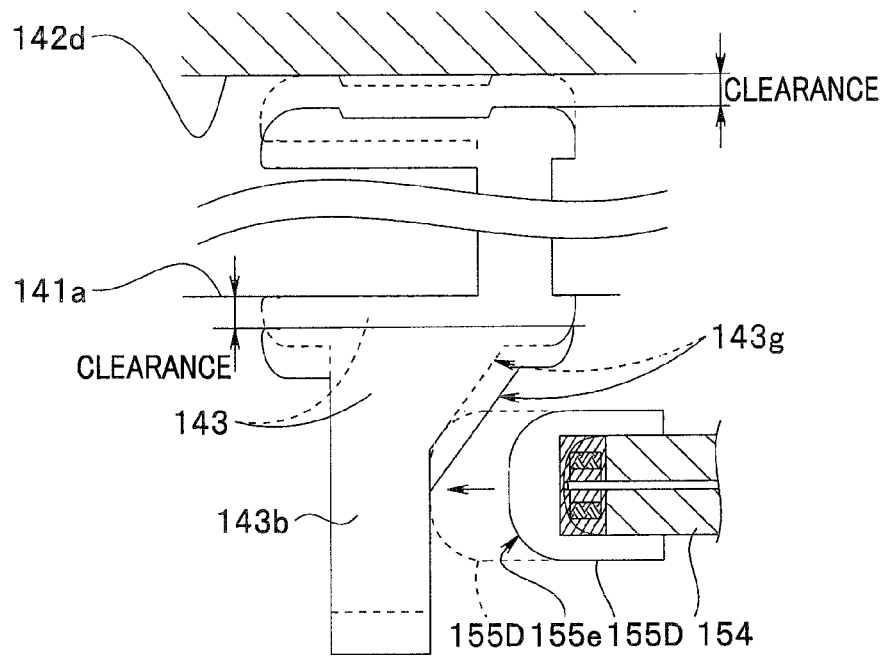
FIG. 38 is a view that illustrates a configuration example of a movable lens frame including a contact member with a distinctively shaped distal end face and a movable frame protrusion corresponding to the contact member, as well as the action thereof according to the tenth embodiment.
Figure 39:
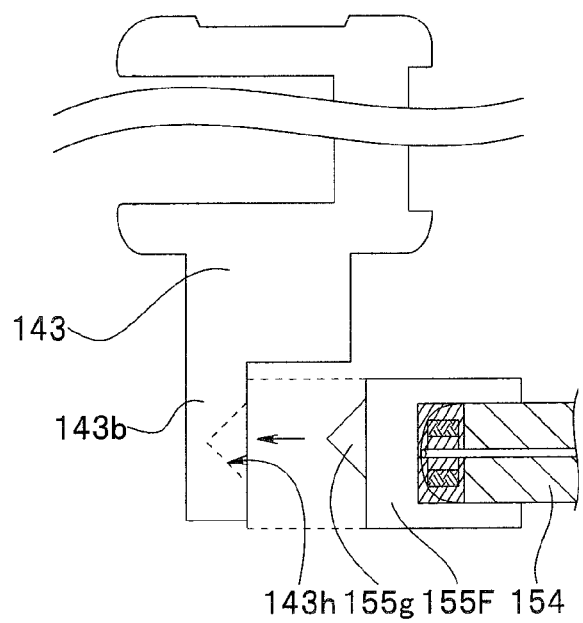
FIG. 39 is a view that illustrates another configuration of a movable lens frame including a contact member with a distinctively shaped distal end face and a movable frame protrusion corresponding to the contact member according to the tenth embodiment.

FIG. 34 to FIG. 39 relate to the tenth embodiment of the present invention. FIG. 34 is a view that describes the configuration of an image pickup unit. FIG. 35 is an enlarged view of a part indicated by arrow XXXV in FIG. 34. FIG. 36 is a view that illustrates a process of fixedly installing a ring member in which an SMA wire is fixed to a contact member. FIG. 37 is a view that illustrates the positional relationship between a contact member and a guide pipe and the positional relationship between the contact member and a movable lens frame when the contact member is disposed at an overheat prevention position. FIG. 38 is a view that illustrates a configuration example of a movable lens frame including a contact member with a distinctively shaped distal end face and a movable frame protrusion corresponding to the contact member, as well as the action thereof. FIG. 39 is a view that illustrates another configuration of a movable lens frame including a contact member with a distinctively shaped distal end face and a movable frame protrusion corresponding to the contact member. In the following description, the same reference numerals are used for components that are the same as components of the endoscope 2 of each of the above described embodiments, and in some cases a detailed description of those components is omitted.

An image pickup apparatus as an image pickup unit of the present embodiment will now be described referring to FIG. 34 to FIG. 37. The image pickup apparatus is disposed inside the distal end portion 12 of the endoscope 2 (see FIG. 1 and FIG. 2).

As shown in FIG. 34, the image pickup apparatus 30 includes a device unit 131 and a lens unit 140.

The device unit 131 principally includes an image pickup device 132, a device frame 133, a circuit board 134, a signal cable 135, and an image pickup apparatus outer frame (hereunder, referred to as "image pickup frame") 136.

The image pickup device 132 is a CCD (Charge Coupled Device), a CMOS (Complementary Metal-Oxide Semiconductor), or the like. For example, cover lenses 137a and 137b that are two optical members are adhesively fixed on the light receiving surface side of the image pickup device 132. The second cover lens 137b is disposed on the light receiving surface of the image pickup device 132.

The device frame 133 is formed of, for example, stainless steel. Of the two cover lenses 137a and 137b that are provided on the light receiving surface side of the image pickup device 132, the first cover lens 137a is integrally fixed by adhesion to the inner surface of the proximal end portion of the device frame 133. More specifically, the image pickup device 132 is fixed to the device frame 133 through the cover lenses 137a and 137b. The proximal end portion of a proximal end side lens frame 142, described later, that is included in the lens unit 140 is arranged at the inner surface of the distal end portion of the device frame 133. After positional adjustment such as focus or the like is completed, the proximal end side lens frame 142 and the device frame 133 are joined by, for example, a solder 121.

The circuit board 134 is, for example, a flexible printed circuit board, which has flexibility. Various electronic components that are not shown in the drawings are mounted on the circuit board 134. The distal end side of the circuit board 134 on which the electronic components are mounted is electrically connected to the image pickup device 132.

A plurality of signal wires 138 are inserted through the inside of the signal cable 135. The distal end portions of the plurality of signal wires 138 are connected to an unshown electric connection portion that is provided in the circuit board 134. The proximal end portion of the signal cable 135 passes through the inside of the insertion portion 7, the operation portion 8, and the universal cord 9 and extends into the inside of the scope connector 10.

The image pickup frame 136 encloses the image pickup device 132, the circuit board 134 on which electronic components are mounted, and a part of the signal cable 135 that is connected to the circuit board 134, and the like. The image pickup frame 136 is, for example, made of stainless steel and is formed in a predetermined shape by rounding or folding one rectangular thin plate. Reference numeral 139 denotes a heat-shrinkable tube that covers the outer surface of the image pickup frame 136 to constitute the exterior of the device unit 131.

Reference numeral 139a denotes an insulative sealing resin. The sealing resin 139a is filled into a space inside the image pickup frame 136 and seals the area surrounding an electrical connection portion between the circuit board 134 and the image pickup device 132, the area surrounding the electronic components mounted on the circuit board 134, the area surrounding the image pickup device 132 and the cover lens 137b, and a connecting portion between the signal cable 135 and the circuit board 134.

As shown in FIG. 34 and FIG. 35, the lens unit 140 is principally composed by a distal end side lens frame 141, the proximal end side lens frame 142, a movable lens frame 143, a distal end position restricting frame 144, a proximal end positional adjustment ring 145, a first movable mechanism portion 151 and a second movable mechanism portion 152.

The first movable mechanism portion 151 is a mechanism that moves the movable lens frame 143 to a magnified observation position as a first observation position, and retains the movable lens frame 143 in that position. The first movable mechanism portion 151 includes a first compression coil spring 146 as a first elastic member and a guide pin 147.

The second movable mechanism portion 152 moves the movable lens frame 143 to a wide-angle observation position as a second observation position. In addition, the second movable mechanism portion 152 serves as a movable lens frame retention mechanism that retains the movable lens frame 143 at a position moved to, and upon release of the retained state, retains a contact member 155, described later, in a condition in which a proximal end face of the contact member 155 is separated by a predetermined distance from a distal end face of a guide pipe 156, described later. The second movable mechanism portion 152 is equipped with a contact member retention mechanism with which the distal end face of the contact member 155 is retained at a position (hereunder, referred to as "overheat prevention position") that is separated by a predetermined distance from the movable lens frame 143 that has moved to the first observation position. Furthermore, the second movable mechanism portion 152 is an actuator that principally includes a second compression coil spring 153 that is a second elastic member, a pipe-like pressing member 154, the contact member 155, the guide pipe 156, and an SMA wire 157.

The distal end side lens frame 141 retains a first optical lens group 161 that includes a plurality of first optical members, and an aperture and the like. The distal end position restricting frame 144 is fixedly arranged in the distal end side lens frame 141.

The proximal end side lens frame 142 retains a second optical lens group 162 as a plurality of second optical members, and an aperture and the like. The second optical lens group 162 and the aperture are provided on the proximal end portion side of the proximal end side lens frame 142. At predetermined positions on the outer circumferential surface of the proximal end side lens frame 142 are provided a male screw portion 142m and a proximal end frame protrusion 142a that protrudes outward from the outer circumferential surface. A through-hole 142b for fixedly installing the guide pipe 156 in parallel with the optical axis is formed in the proximal end frame protrusion 142a.

The movable lens frame 143 retains at least one optical lens 163. The movable lens frame 143 has an engaging portion 143a that is engagedly inserted into the outer circumferential surface of the rear end of the distal end side lens frame 141 on, for example, the distal end side.

A movable frame protrusion 143b that protrudes outward from the outer circumferential surface is provided on the engaging portion 143a of the movable lens frame 143. A sliding hole 143c through which one end of the guide pin 147 passes and a concave portion 143d in which one end of the first compression coil spring 146 is disposed are formed in the movable frame protrusion 143b. The movable frame protrusion 143b protrudes to the outer side of the circumferential surface of the proximal end side lens frame 142 via a notch groove 142c that is formed as far as a midway section from the distal end of the outer circumferential surface on the distal end side of the proximal side lens frame 142. The distal end face and proximal end face of the movable frame protrusion 143b are configured as a front side positioning face 143f and a rear side positioning face 143r.

The distal end position restricting frame 144 is joined by, for example, an adhesive 122 to the outer circumferential surface of the distal end side lens frame 141. A distal end portion 142d of the proximal end side lens frame 142 is disposed inside a concave portion 144a of the distal end position restricting frame 144. The distal end portion 142d is joined by, for example, an adhesive 123 to the inside of the concave portion 144a.

A stepped hole 144b is formed on the distal end side of the distal end position restricting frame 144. The stepped hole 144b includes a convex portion 144c and a pinhole 144d. The diameter dimensions of the pinhole 144d are smaller than the external diameter of the convex portion 144c. The other end of the guide pin 147 is fixed in the pinhole 144d. The other end of the first compression coil spring 146 is disposed in the convex portion 144c. The guide pin 147 is arranged parallel to the optical axis.

The first compression coil spring 146 has an urging force that causes the movable lens frame 143 to contact against the proximal end positional adjustment ring 145 that sets a magnified observation position, and also maintains that state. The guide pin 147 that protrudes from the pinhole 144d is inserted through the first compression coil spring 146. By inserting the guide pin 147 through the inside of the first compression coil spring 146, buckling or the like of the first compression coil spring 146 is prevented. Further, by inserting one end of the guide pin 147 through the sliding hole 143c, the movable lens frame 143 can guide the guide pin 147 to move smoothly in the axial direction. More specifically, according to the present embodiment the guide pin 147 serves as a mechanism that prevents buckling of the compression coil spring 146 and also as a guide mechanism that guides the movement of the movable lens frame 143.

The proximal end positional adjustment ring 145 has, on the inner circumferential surface thereof, a female screw portion 145f that meshes with the male screw portion 142m of the proximal end side lens frame 142. The distal end face of the proximal end positional adjustment ring 145 constitutes a movable lens frame proximal end restricting face 145a that the rear side positioning face 143r of the movable frame protrusion 143b included in the movable lens frame 143 contacts against. The proximal end positional adjustment ring 145 is a member that sets a magnified observation position, and is fixed with, for example, an adhesive, after performing positional adjustment such as focus by rotation.

The guide pipe 156 includes an inner hole 156i. The second compression coil spring 153, one end of the pressing member 154, and the distal end portion of the insulating tube 158 are arranged in the inner hole 156i. The second compression coil spring 153 and the pressing member 154 are slidably arranged in the inner hole 156i. The insulating tube 158 is fixed by, for example, an adhesive in the inner hole 156i.

The distal end portion of the cover tube 159 is covered over the outer circumferential surface of the guide pipe 156 from the proximal end side to a midway portion thereof. The cover tube 159 covers the outer circumference of the insulating tube 158 and an electric cable 160 that is described later.

The distal end side of the guide pipe 156 is disposed in the through-hole 142b formed in the proximal end frame protrusion 142a of the proximal end side lens frame 142. At this time, the distal end face 156a of the guide pipe 156 protrudes by a predetermined amount from the distal end face 142f of the proximal end frame protrusion 142a and is fixed by a solder or an adhesive. A proximal end face 155r of the contact member 155 contacts against the distal end face 142f.

The second compression coil spring 153 that is disposed in the inner hole 156i of the guide pipe 156 has an urging force that is greater than the urging force of the first compression coil spring 146. More specifically, the second compression coil spring 153 is equipped with an urging force that, in a state in which the first compression coil spring 146 is urging the movable lens frame 143, causes the front side positioning face 143f of the movable lens frame 143 to contact against the distal end position restricting frame 144 against the urging force of the first compression coil spring 146 and maintains that state. The movable lens frame 143 is disposed in a wide-angle observation position by the front side positioning face 143f of the movable frame protrusion 143b of the movable lens frame 143 contacting against the distal end position restricting frame 144.

The pressing member 154 disposed in the inner hole 156i of the guide pipe 156 has a tubular shape. The contact member 155 that is formed in a cylindrical shape with an insulating member is fixedly provided at the distal end portion of the pressing member 154. The SMA wire 157 that is inserted and guided through a through-hole 158a of the insulating tube 158 and the inside of the second compression coil spring 153 passes through a through-hole 154a of the pressing member 154.

The SMA wire 157 has properties such that the SMA wire 157 contracts upon heating when an electric current is applied thereto, and expands upon cooling (natural cooling to ordinary temperature) when application of the electric current is stopped.

A midway section 157m on the distal end side of the SMA wire 157 that is led out from the through-hole 154a of the pressing member 154 is bent into a predetermined state, as shown in FIG. 36, after passing through a hole 164a of the ring member 164, and the distal end side of the SMA wire 157 is extended from the side of the ring member 164 and fixed with an adhesive 124. The ring member 164 on which the SMA wire 157 has been fixed is fixedly provided in the contact member 155.

As shown in FIG. 36, the contact member 155 includes a pressing member fixing portion 155a that is a concave space, and a notch 155c that is formed from an opening 155b side to a midway section on the side circumferential surface. The notch 155c communicates the pressing member fixing portion 155a with the outside.

Next, a contact member fixing process in which the ring member 164 to which the midway section 157m of the SMA wire 157 is fixed is disposed inside the pressing member fixing portion 155a of the contact member 155 and the contact member 155 is fixed in an externally fitting state to the distal end portion of the pressing member 154 is described.

First, the SMA wire 157 that is led out from the hole 164a of the ring member 164 is inserted through the through-hole 154a of the pressing member 154. The ring member 164 is then disposed at the distal end face of the pressing member 154.

Next, an adhesive is applied to the distal end of the pressing member 154 and the ring member 164. As shown in FIG. 35 that is an enlarged view of the area indicated by arrow XXXV in FIG. 34, the ring member 164 and the distal end portion of the pressing member 154 are disposed inside the pressing member fixing portion 155a. At this time, the SMA wire 157 that extends from the side of the ring member 164 is disposed in advance in the notch 155c.

Thereafter, by curing of the adhesive, as shown in FIG. 34 and FIG. 35, the contact member 155, the ring member 164 and SMA wire 157, and the pressing member 154 are integrally fixed. In this fixed state, the distal end side of the SMA wire 157 extends to outside from the notch 155c of the contact member 155. It is therefore possible to prevent the SMA wire 157 from being disposed on the proximal end face 155r side.

Thus, the pressing member 154 is constituted with the contact member 155 fixed at the distal end portion thereof. The pressing member 154 is disposed inside the inner hole 156i of the guide pipe 156 in which the second compression coil spring 153 is provided.

In this connection, instead of forming the notch 155c on the side circumferential surface of the contact member 155, a configuration may be adopted in which a through-hole is formed that communicates the pressing member fixing portion 155a and the outside. By adopting such a configuration, it is possible to reliably prevent the SMA wire 157 being disposed on the proximal end face 155r side.

Further, the distal end portion of the SMA wire 157 that is led to outside of the contact member 155 is passed through the inside of an unshown insulating tube and is connected to, for example, an unshown signal wire for grounding that is passed through the proximal end side of the bending portion 13 that is included in the insertion portion 7 of the endoscope 2 shown in FIG. 1.

The proximal end of the SMA wire 157 is disposed on the proximal end side of the bending portion 13 that is included in the insertion portion 7 of the endoscope 2. An electric wire 160a that is passed through an electric cable 160 that supplies an electric current to the SMA wire 157 is connected, for example, through a caulking member 165 to the proximal end of the SMA wire 157. Accordingly, by applying an electric current to the SMA wire 157 via the electric cable 160 from a power supply portion provided in the video processor 5, the temperature of the SMA wire 157 increases and the SMA wire 157 contracts.

The process of assembling the lens unit 140 will now be described.

First, a process in which frames 141, 142, 143, and 144, ring 145, and the first movable mechanism portion 151 are assembled to construct a frame body is described.

When constructing the frame body, the distal end position restricting frame 144 is fixed to the distal end side lens frame 141. At this time, one end of the guide pin 147 is fixedly arranged in advance in the pinhole 144d. Further, the proximal end positional adjustment ring 145 is screwed into the male screw portion 142m of the proximal end side lens frame 142.

Next, the first compression coil spring 146 is disposed in the guide pin 147 that is provided in the distal end position restricting frame 144 that has been fixed to the distal end side lens frame 141. The movable lens frame 143 is then arranged on the rear end side of the distal end side lens frame 141. At this time, the guide pin 147 is passed through the sliding hole 143c formed in the movable frame protrusion 143b of the movable lens frame 143, and the first compression coil spring 146 is disposed inside the concave portion 143d.

Subsequently, the distal end portion 142d of the proximal end side lens frame 142 to which the proximal end positional adjustment ring 145 is mounted is disposed inside the concave portion 144a of the distal end position restricting frame 144. At this time, the movable frame protrusion 143b of the movable lens frame 143 is disposed in the notch groove 142c formed in the proximal end side lens frame 142. Thereafter, the proximal end side lens frame 142 and the distal end position restricting frame 144 are fixed by, for example, the adhesive 122.

Thus, a frame body is constructed in which the optical lens 163 between the first optical lens group 161 and the second optical lens group 162 is arranged in a movable condition. In this frame body, the movable lens frame 143 is moved to the second optical lens group 162 side of the proximal end side lens frame 142 by the urging force of the first compression coil spring 146. At this time, the rear side positioning face 143r of the movable frame protrusion 143b provided in the movable lens frame 143 contacts against the movable lens frame proximal end restricting face 145a of the proximal end positional adjustment ring 145. In this case, the position of the proximal end positional adjustment ring 145 is adjusted, and the position of the optical lens 163 is decided. After completing the positional adjustment, the proximal end positional adjustment ring 145 and the proximal end side lens frame 142 are integrally fixed.

Next, a process for mounting the second movable mechanism portion 152 to the frame body to construct the lens unit 140 is described.

First, when constructing the lens unit 140, the guide pipe 156 in which the insulating tube 158 and the cover tube 159 are fixed and through which the SMA wire 157 passes is prepared.

Next, the guide pipe 156 is disposed in the through-hole 142b of the proximal end side lens frame 142. The amount of protrusion of the distal end face 156a of the guide pipe 156 from the distal end face 142f of the proximal end frame protrusion 142a is fixed by taking into consideration the position of the proximal end positional adjustment ring 145, that is, a movement distance of the movable lens frame as denoted by reference characters L1 in FIG. 35.

At this time, the amount of protrusion is adjusted so that a movement distance of the contact member as denoted by reference character L2 in FIG. 35 is longer by a predetermined amount that is previously set than the movement distance of the movable lens frame that is denoted by reference character L1.

This is done so that, in a state in which the proximal end face 155r of the contact member 155 contacts against the distal end face 156a of the guide pipe 156 as shown by the solid line, when the rear side positioning face 143r of the movable frame protrusion 143b provided in the movable lens frame 143 contacts against the movable lens frame proximal end restricting face 145a of the proximal end positional adjustment ring 145, as shown by the chain double-dashed line, by providing a preset clearance t between a rear face 143e of the movable frame protrusion 143b and a distal end face 155f of the contact member 155, the movable frame protrusion 143b is prevented from contacting against the contact member 155 and hindering movement of the movable lens frame 143 to the magnified observation position.

Subsequently, the second compression coil spring 153 is disposed inside the inner hole 156i of the guide pipe 156 that is integrated with the proximal end side lens frame 142. At this time, the SMA wire 157 is passed through the inner hole of the second compression coil spring 153.

Next, the SMA wire 157 is passed through the through-hole 154a from the proximal end side of the pressing member 154, and the midway section 157m of the SMA wire 157 that is led out from the through-hole 154a on the distal end side is fixed to the ring member 164. In accordance with the contact member fixing process described above, the ring member 164 to which the SMA wire 157 is fixed is disposed inside the pressing member fixing portion 155a of the contact member 155 and the contact member 155 is fixed to the distal end portion of the pressing member 154.

That is, first the ring member 164 is disposed on the distal end face of the pressing member 154. At this time, the proximal end side of the SMA wire 157 is pulled to remove any slackness. An adhesive is then applied to the distal end of the pressing member 154 and the ring member 164. Next, the SMA wire 157 is matched with the notch 155c, and the ring member 164 and the distal end portion of the pressing member 154 are disposed in the pressing member fixing portion 155a.

Subsequently, the proximal end side of the pressing member 154 having the contact member 155 provided at the distal end portion thereof is pushed into the inner hole 156i against the urging force of the second compression coil spring 153. Thereafter, the distal end face 155f of the contact member 155 is disposed on the rear face 143e side of the movable frame protrusion 143b.

When the distal end face 155f is disposed at the rear face 143e, the pressing member 154 moves due to the urging force of the second compression coil spring 153. Thereupon, the distal end face 155f of the contact member 155 contacts against the rear face 143e, and the movable lens frame 143 that had been disposed at the magnified observation position by the urging force of the second compression coil spring 153 is moved to the wide-angle observation position. The front side positioning face 143f of the movable frame protrusion 143b then contacts against the distal end position restricting frame 144, so that the movable lens frame 143 is disposed at the wide-angle observation position that is the normal observation position. In this state the adhesive is allowed to cure. Thus, construction of the lens unit 140 is completed when the adhesive has cured. According to the lens unit 140, when an electric current is not being applied to the SMA wire 157, the movable lens frame 143 is disposed at the wide-angle observation position by the urging force of the second compression coil spring 153.

According to the lens unit 140, a configuration is adopted in which the SMA wire 157 is folded back inside the pressing member fixing portion 155a of the contact member 155 that is formed with an insulating member, and is led out from the side face of the contact member 155. It is therefore possible to secure insulation between the SMA wire 157 and the movable lens frame 143, and also prevent the SMA wire 157 from being disposed on the proximal end face 155r side.

Next, an operation check is performed on the lens unit 140, and acquisition of a calibration value and overheat prevention position information is carried out.

The term "calibration value" refers to a resistance value of the SMA wire 157 when the proximal end face 155r of the contact member 155 has arrived at (contacts against) the distal end face 156a of the guide pipe 156. The term "overheat prevention position information" refers to a resistance value that causes the contact member 155 to be disposed at the overheat prevention position during magnified observation. As shown in FIG. 37, by disposing the contact member 155 at the overheat prevention position, the proximal end face 155r of the contact member 155 is separated by a first separation distance (t1) from the distal end face 156a of the guide pipe 156, and the distal end face 155f of the contact member 155 is separated by a second separation distance (t2) from the rear face 143e of the movable frame protrusion 143b of the movable lens frame 143. These separation distances t1 and t2 are values that are set based on the clearance t.

To perform an operation check, first the distal end side and the proximal end of the SMA wire 157 are connected, and an electric current is applied to the SMA wire 157 from the power supply portion. Thereupon, the SMA wire 157 starts to contract accompanying a rise in the temperature thereof. Accompanying the contraction of the SMA wire 157, the pressing member 154 provided with the contact member 155 that has been retaining the movable lens frame 143 at the wide-angle observation position under the urging force of the second compression coil spring 153 is moved in the proximal end direction, that is, the magnified observation direction. In other words, when an electric current is applied, the SMA wire 157 causes the pressing member 154 on which the contact member 155 is fixedly provided to move in the proximal end direction against the urging force of the second compression coil spring 153. Thus, as described above, the movable lens frame 143 moves in the magnified observation position direction under the urging force of the first compression coil spring 146.

Further, through the increase in temperature of the SMA wire 157, the proximal end face 155r of the contact member 155 moves closer to the distal end face 156a of the guide pipe 156. At this time, the resistance value decreases together with the temperature increase.

When the proximal end face 155r of the contact member 155 contacts against the distal end face 156a of the guide pipe 156, accompanying that contact, contraction of the SMA wire 157 stops irrespective of the temperature increase. More specifically, the resistance value no longer changes. The resistance value at this time is a value that notifies the operator that the proximal end face 155r of the contact member 155 is in a state of abutting against the distal end face 156a of the guide pipe 156. This resistance value is acquired as the calibration value. Furthermore, based on the calibration value, a resistance value that causes the proximal end face 155r of the contact member 155 to stop a predetermined distance before the distal end face 156a of the guide pipe 156 is acquired as the overheat prevention position information.

In this case, the SMA wire 157 is controlled with the resistance value that is acquired as the overheat prevention position information so that the SMA wire 157 is contracted. It is then confirmed whether or not the contact member 155 is disposed at the overheat prevention position. More specifically, it is confirmed whether or not a predetermined clearance is formed without the contact member 155 contacting against the distal end face 156a of the guide pipe 156 and the rear face 143e of the movable lens frame 143.

When it is confirmed that the contact member 155 is disposed at the overheat prevention position, application of the electric current to the SMA wire 157 is stopped, and switching of the observation position is confirmed. At this time, in the case where the contact member 155 is disposed at the overheat prevention position, when the application of electric current to the SMA wire 157 is stopped, the SMA wire 157 starts to expand accompanying natural cooling. Thereupon, the movable lens frame 143 is moved to the wide-angle observation position from the magnified observation position by the urging force of the second compression coil spring 153.

Thereafter, the calibration value and the overheat prevention position information are registered as specific values of the lens unit 140 in the memory of the endoscope 2 in which the lens unit 140 is to be mounted.

When performing an endoscopic examination with the endoscope 2 on which the above described lens unit 140 is mounted, prior to the examination the user performs a calibration process that causes the proximal end face 155r of the contact member 155 to contact against the distal end face 156a of the guide pipe 156. At a control portion (unshown) of the endoscope system 1, a resistance value acquired at the time of the calibration process is compared with the calibration value registered in the memory. At this time, when the comparison result is "no abnormality", the resistance of the SMA wire 157 is controlled so that the contact member 155 is disposed at the overheat prevention position at the time of magnified observation based on the overheat prevention position information registered in the memory. In this connection, if the comparison result is "abnormality exists", the user is notified, and the user carries out maintenance of the endoscope.

Thus, by acquiring a calibration value and overheat prevention position information for each individual lens unit 140, at the time of magnified observation the resistance value of the SMA wire 157 is controlled based on the overheat prevention position information to dispose the contact member 155 at the overheat prevention position at which the contact member 155 does not contact against the guide pipe 156 and the movable lens frame 143, so that overheating of the SMA wire 157 can be prevented.

As a result, when application of an electric current to the SMA wire 157 is stopped during endoscopic observation in order to switch from magnified observation to wide-angle observation, expansion of the SMA wire 157 can be started simultaneously with the start of natural cooling, thus enabling the optical properties to be smoothly changed. In other words, the expansion responsiveness when the user enters an instruction to vary the optical properties is enhanced and the optical properties can be changed at the timing of that instruction.

Further, by assigning contraction of the SMA wire 157 to the release of the urging force of the second compression coil spring 153 when switching from wide-angle observation to magnified observation, the optical properties can be smoothly changed by the first compression coil spring 146 after releasing the urging force of the second compression coil spring 153.

Thus, by expanding and contracting of the SMA wire 157, movement of the movable lens frame 143 to the proximal end side and the distal end side can be performed stably and rapidly using the urging forces of the two kinds of compression coil springs 146 and 153 without directly moving the movable lens frame 143.

Further, the movable lens frame 143 is retained at the magnified observation position using the urging force of the first compression coil spring 146 and is retained at the wide-angle observation position using the urging force of the second compression coil spring 153. It is therefore possible to solve the problem whereby the position of the movable lens frame 143 changes during observation due to the SMA wire 157 contracting or expanding because of a change in the temperature of the SMA wire 157.

Further, when the application of an electric current to the SMA wire 157 is stopped during observation, because the SMA wire 157 expands, the movable lens frame 143 is disposed at the wide-angle observation position by the urging force of the second compression coil spring 153. Therefore, even when application of the electric current to the SMA wire 157 is stopped, it is possible to continue observation using a wide angle.

In the above described embodiment, a configuration is adopted in which the distal end face 155f of the contact member 155 is contacted against the rear face 143e of the movable frame protrusion 143b of the movable lens frame 143. However, by configuring a contact member and a movable frame protrusion as shown in FIG. 38 and FIG. 39, and pressing and retaining in a desired direction the movable lens frame having a clearance, it is possible to prevent vignetting of images due to displacement of the core of the optical lens 163 provided in the movable lens frame.

FIG. 38 is a view that illustrates a configuration example of a movable lens frame including a contact member with a distinctively shaped distal end face and a movable frame protrusion corresponding to the contact member, as well as the action thereof. FIG. 39 is a view that illustrates another configuration of a movable lens frame including a contact member with a distinctively shaped distal end face and a movable frame protrusion corresponding to the contact member.

As shown in FIG. 38, a contact member 155D of the present embodiment has a curved surface portion 155e as a movable lens frame restricting portion at the distal end portion thereof. In contrast, the movable frame protrusion 143b of the movable lens frame 143 includes an inclined face 143g as a movable lens frame restricting portion that the curved surface portion 155e contacts against. According to this configuration, the curved surface portion 155e contacts against the inclined face 143g when the movable lens frame 143 is retained at the wide-angle observation position by the urging force of the second compression coil spring 153.

Thus, the movable lens frame 143 is moved as indicated by the broken lines within the range of the clearance and contacts against the outer circumferential surface on the rear end side of the distal end side lens frame 141 or the inner circumferential surface of the distal end portion 142d of the proximal end side lens frame 142. It is therefore possible to prevent image vignetting that arises due to the position of the optical lens 163 being displaced during observation.

In this connection, as shown in FIG. 39, a configuration may also be adopted in which the contact member 155F is provided with a movable lens frame restricting portion and, for example, a cone-shaped portion 155g, and the movable frame protrusion 143b is provided with an insertion hole 143h into which the cone-shaped portion 155g is engageably inserted. According to this configuration, when the movable lens frame 143 is retained at the wide-angle observation position by the urging force of the second compression coil spring 153, the cone-shaped portion 155g is engageably inserted inside the insertion hole 143h and the same action as described above can be obtained.

In this connection, the configuration is not limited to a curved surface portion and an inclined face, or cone-shaped concave and convex portions or the like, but a hemispherical portion, a tapered portion or the like may also be used.

As described in the foregoing, according to the present invention the assemblability to a distal end portion of an image pickup apparatus of an electronic endoscope equipped with a focusing function and the like can be improved, and an image pickup apparatus that can prevent a displacement of the photographing optical axis of a lens provided in a lens frame that moves as well as an electronic endoscope equipped with the image pickup apparatus can be provided.

Further, according to the configuration of the lens unit of the present invention, when a shape memory alloy wire is expanded in a non-tensile state, by an urging force of a second elastic member, a movable lens frame is retained at a second observation position by the pressing force of a pressing member having a contact member fixed to a distal end portion thereof. In contrast, when the shape memory alloy wire is switched to a contraction state, the pressing member moves to the proximal end accompanying the start of contraction. Thereupon, the pressing force from the pressing member that had been acting on the movable lens frame is released, and the movable lens frame moves to the proximal end side under the urging force of a first elastic member. When the contact member is moved to and retained at a position at which the proximal end face of the contact member is separated by a predetermined distance from the distal end face of the guide pipe and, furthermore, the distal end face of the contact member is separated by a predetermined distance from the movable lens frame that has moved to the first observation position, the movable lens frame is retained at the first observation position. Thereafter, when the shape memory alloy wire is switched from the contraction state to an expansion state, at substantially the same time as the start of expansion by natural cooling, the movable lens frame is moved to the second observation position by the urging force of the second elastic member.

The invention described in the foregoing embodiments is not limited to those embodiments and modification examples, and various changes and modifications and the like are possible at the implementation stage without deviating from the spirit and scope of the present invention. Further, the embodiments include inventions of various stages, and various inventions can be extracted by appropriately combining a plurality of the disclosed configuration requirements.

For example, if a problem described herein as a problem to be overcome by the invention can be solved and if the effects described herein are still obtained after omitting some of the configuration requirements shown in the embodiments, then the configuration obtained by omitting the configuration requirements can be extracted as an embodiment of the invention.

What is claimed is:

1. An image pickup apparatus that varies optical properties by moving a part of lenses of an objective lens, the image pickup apparatus comprising:
    a solid-state image pickup device unit that is arranged at a rear-end section and that subjects a subject image to photoelectric conversion;
    a fixed lens frame that retains the objective lens that is disposed to the front of the solid-state image pickup device unit;
    a movable lens frame that retains the part of lenses that moves along a photographing optical axis inside the fixed lens frame; and
    an actuator that moves the movable lens frame forward and backward, the actuator including:
        a rod-shaped rigid member that has one end connected to the movable lens frame;
        a shape memory alloy that is coupled to the rod-shaped rigid member;
        a guide pipe into which the rod-shaped rigid member is insertedly fitted in a condition in which the rod-shaped rigid member can move forward and backward, the guide pipe being fixed to the fixed lens frame and rectilinearly guiding the rod-shaped rigid member in a photographing optical axis direction of the solid-state image pickup device unit; and
        a fixing member that fixes an axial position of the guide pipe in the fixed lens frame in a condition in which the axial position of the guide pipe can be varied within a clearance in a circumferential direction of the guide pipe, the clearance being formed between the guide pipe and the fixed lens frame.

2. An electronic endoscope comprising:
an insertion portion that is inserted into a subject/object to be examined and
an image pickup apparatus that varies optical properties by moving a part of lenses of an objective lens that is contained in the insertion portion and that observes inside the subject/object to be examined by means of the image pickup apparatus, wherein the image pickup apparatus comprises:
    a solid-state image pickup device unit that is arranged at a rear-end section and that subjects a subject image to photoelectric conversion;
    a fixed lens frame that retains the objective lens that is disposed to the front of the solid-state image pickup device unit;
    a movable lens frame that retains the part of lenses that moves along a photographing optical axis inside the fixed lens frame; and
    an actuator that moves the movable lens frame forward and backward, the actuator including:
        a rod-shaped rigid member that has one end connected to the movable lens frame;
        a shape memory alloy that is coupled to the rod-shaped rigid member;
        a guide pipe into which the rod-shaped rigid member is insertedly fitted in a condition in which the rod-shaped rigid member can move forward and backward, the guide pipe being fixed to the fixed lens frame and rectilinearly guiding the rod-shaped rigid member in a photographing optical axis direction of the solid-state image pickup device unit; and
        a fixing member that fixes an axial position of the guide pipe in the fixed lens frame in a condition in which the axial position of the guide pipe can be varied within a clearance in a circumferential direction of the guide pipe, the clearance being formed between the guide pipe and the fixed lens frame.

\* \* \* \* \*